(12) United States Patent
Cohen et al.

(10) Patent No.: US 8,865,769 B2
(45) Date of Patent: Oct. 21, 2014

(54) BACLOFEN AND ACAMPROSATE BASED THERAPY OF NEUROLOGICAL DISORDERS

(71) Applicant: PHARNEXT, Issy les Moulineaux (FR)

(72) Inventors: Daniel Cohen, Le Vesinet (FR); Ilya Chumakov, Vaux le Penil (FR); Serguei Nabirochkin, Chatenay Malabry (FR); Emmanuel Vial, Paris (FR); Mickael Guedj, Paris (FR)

(73) Assignee: Pharnext, Issy les Moulineaux (FR)

( * ) Notice: Subject to any disclaimer, the term of this patent is extended or adjusted under 35 U.S.C. 154(b) by 0 days.

(21) Appl. No.: 13/691,981

(22) Filed: Dec. 3, 2012

(65) Prior Publication Data

US 2013/0085122 A1   Apr. 4, 2013

Related U.S. Application Data

(63) Continuation of application No. PCT/EP2012/053570, filed on Mar. 1, 2012.

(60) Provisional application No. 61/468,658, filed on Mar. 29, 2011, provisional application No. 61/493,606, filed on Jun. 6, 2011.

(30) Foreign Application Priority Data

Mar. 1, 2011 (EP) .................................... 11305217
Jun. 6, 2011 (EP) .................................... 11305687

(51) Int. Cl.
| | |
|---|---|
| *A61K 31/185* | (2006.01) |
| *A61K 31/205* | (2006.01) |
| *A61K 31/13* | (2006.01) |
| *A61K 31/445* | (2006.01) |
| *A61K 31/42* | (2006.01) |
| *A61K 31/44* | (2006.01) |
| *A61K 31/195* | (2006.01) |
| *A61K 31/138* | (2006.01) |
| *A61K 31/164* | (2006.01) |
| *A61K 31/197* | (2006.01) |
| *A61K 45/06* | (2006.01) |
| *A61K 31/137* | (2006.01) |
| *A61K 31/64* | (2006.01) |
| *A61K 31/145* | (2006.01) |

(52) U.S. Cl.
CPC ............ *A61K 31/197* (2013.01); *A61K 31/445* (2013.01); *A61K 31/42* (2013.01); *A61K 31/44* (2013.01); *A61K 31/195* (2013.01); *A61K 31/185* (2013.01); *A61K 31/138* (2013.01); *A61K 31/164* (2013.01); *A61K 45/06* (2013.01); *A61K 31/137* (2013.01); *A61K 31/64* (2013.01); *A61K 31/145* (2013.01)
USPC ............ 514/567; 514/555; 514/568; 514/665

(58) Field of Classification Search
USPC ............ 514/171, 567, 255.01, 380, 347, 317, 514/247, 378, 319, 479
See application file for complete search history.

(56) References Cited

U.S. PATENT DOCUMENTS

| | | | |
|---|---|---|---|
| 6,391,922 | B1 | 5/2002 | Fogel |
| 8,741,886 | B2 | 6/2014 | Cohen et al. |
| 2001/0004640 | A1 | 6/2001 | Inada et al. |
| 2001/0023246 | A1 | 9/2001 | Barritault et al. |
| 2004/0102525 | A1 | 5/2004 | Kozachuk |
| 2008/0188510 | A1 | 8/2008 | Yoshino |
| 2009/0069419 | A1 | 3/2009 | Jandeleit et al. |
| 2009/0197958 | A1 | 8/2009 | Sastry et al. |
| 2011/0230659 | A1 | 9/2011 | Tsukamoto et al. |
| 2012/0270836 | A1 | 10/2012 | Cohen et al. |

FOREIGN PATENT DOCUMENTS

| | | |
|---|---|---|
| EP | 1 563 846 | 8/2005 |
| EP | 1 837 034 | 9/2007 |
| WO | WO 01/58476 | 8/2001 |
| WO | WO 03/007993 | 1/2003 |
| WO | WO 03/080068 | 10/2003 |
| WO | WO 2007/053596 | 5/2007 |
| WO | WO 2008/006070 | 1/2008 |
| WO | WO 2008/143361 | 11/2008 |
| WO | WO 2009/133128 | 11/2009 |
| WO | WO 2009/133141 | 11/2009 |
| WO | WO 2009/133142 | 11/2009 |
| WO | WO 2010/061931 | 6/2010 |
| WO | WO 2011/054759 | 5/2011 |

OTHER PUBLICATIONS

Colombo et al. Role of GABA(B) receptor in alcohol dependence: reducing effect of baclofen on alcohol intake and alcohol motivational properties in rats and amelioration of alcohol withdrawl syndrome and alcohol craving in human alcoholics. Neurotoxicity research, 2004, vol. 6, No. 5 p. 403-414 abstract.*

Soyka Efficacy of acamprostate in the relapse prevention of alcohol dependence. Results of clinical trials and therapeutical propospects. Nervenheilkunde, 1995 vol. 14, No. 2 pp. 83-86. abstract.*

(Continued)

*Primary Examiner* — Jennifer M Kim
(74) *Attorney, Agent, or Firm* — Saliwanchik, Lloyd & Eisenschenk

(57) ABSTRACT

The present invention relates to combinations and methods for the treatment of neurological disorders related to glutamate excitotoxicity and Amyloid β toxicity. More specifically, the present invention relates to novel combinatorial therapies of Multiple Sclerosis, Alzheimer's disease, Alzheimer's disease related disorder, Amyotrophic Lateral Sclerosis, Parkinson's disease, Huntington's disease, neuropathic pain, alcoholic neuropathy, alcoholism or alcohol withdrawal, or spinal cord injury, based on Baclofen and Acamprosate combination.

10 Claims, 18 Drawing Sheets

(56) References Cited

OTHER PUBLICATIONS

Binbay et al. The efficacy of donepezil in two cases with alcohol induced Korsakoff's syndrome. Klinik Pasikofarmakoloji Bulteni (2008) vol. 18, No. 1, pp. 46-49. abstract.*

Flannery et al. Baclofen for alcohol dependence: A preliminary open-label study Alcoholism: Clinical and experimental research vol. 28, No. 10 Oct. 2004 pp. 1517-1523.*

Hama, A. et al. "Synergistic interaction between intrathecal gamma-aminobutyrate (GABA) receptor agonists and an N-methyl-D-aspartate (NMDA) receptor antagonist in rats with neuropathic spinal cord injury pain" *Society for Neuroscience abstract viewer and in Itinerary Planner*, 2010, p. 1, vol. 40.

Lyden, P.D. et al. "Combination therapy protects ischemic brain in rats. A glutamate antagonist plus a gamma-aminobutyric acid agonist" *Stroke*, 1994, pp. 189-196, vol. 25.

Costa, C. et al. "Coactivation of $GABA_A$ and $GABA_B$ Receptor Results in Neuroprotection During in Vitro Ischemia" *Stroke*, Jan. 15, 2004, pp. 596-600, vol. 35.

Zhou, C. et al. "Neuroprotection of Y-Aminobutyric Acid Receptor Agonists Via Enhancing Neuronal Nitric Oxide Synthase (Ser847) Phosphorylation Through Increased neuronal Nitric Oxide Synthase and PSD95 Interaction and Inhibited Protein Phosphatase Activity in Cerebral Ischemia" *Journal of Neuroscience Research*, 2008, pp. 2973-2983, vol. 86.

Louzada, P. R. et al. "Taurine prevents the neurotoxicity of β-amyloid and glutamate receptor agonists: activation of GABA receptors and possible implications for Alzheimer's disease and other neurological disorders" *The FASEB Journal*, Mar. 2004, vol. 18.

Engelhard, K. et al. "Der neuroprotektive Einfluss des Glutamat-Antagonisten Acamprosat nach experimenteller zerebraler Ischämie" *Der Anaesthesist*, Sep. 22, 2000, pp. 816, 818, and 820, vol. 49, No. 9.

Akan, P. et al., "Pregnenolone protects the PC-12 cell line against amyloid beta peptide toxicity but its sulfate ester does not" *Chemico-Biological Interactions*, 2009, pp. 65-70, vol. 177, No. 1, XP-002613421.

Andrieu, S. et al. "Association of Alzheimer's Disease Onset With Ginkgo Biloba and Other Symptomatic Cognitive Treatments in a Population of Woman Aged 75 Years and Older From the EPIDOS Study" *Journal of Gerontology: Medical Sciences*, Apr. 2003, pp. 372-377, vol. 58A, No. 4, XP-009144763.

Aplin, A. C. et al. "Vascular regression and survival are differentially regulated by MT1-MMP and TIMPs in the aortic ring model of angiogenesis" *Am. J. Physiol Cell Physiol*, Aug. 2009, pp. C471-C480, vol. 297, No. 2, XP-002613424.

Dobrek, L. et al. "Future Potential Indications for Pharmacotherapy Using Renin-Angiotensin-Aldosterone System inhibitory Agents" *Adv. Clin. Exp. Med.*, May 2010, pp. 389-398, vol. 19, No. 3, XP-009144580.

Finsterer, J. et al. "Neurotoxocarosis" *Rev. Inst. Med. Trop. S. Paulo*, pp. 279-287, Sep.-Oct. 2007, vol. 49, No. 5, XP-002623261.

Kakinuma, Y. et al. "Donepezil, an acetylcholinesterase inhibitor against Alzheimer's dementia, promotes angiogenesis in an ischemic hindlimb model" *Journal of Molecular and Cellular Cardiology*, Apr. 2010, pp. 680-693, vol. 48, No. 4, XP-26949580.

Klein, H.E. at al, "Calcium antagonists in dementias. Assessment of the therapeutic efficacy" *Munchener Medizinische Wochenschrift*, 1995, pp. 38, 41-43, vol. 137, No. 47, XP-001525484.

Lee, S.T. et al. "Reduced circulating angiogenic cells in Alzheimer disease" *Neurology*, May 1, 2009, pp. 1858-1863, vol. 72, No. 21, XP-002610857.

Lu, Y. at al. "Neuroprotective activity and evaluation of Hsp90 inhibitors in an immortalized neuronal cell line" *Bioorganic & Medicinal Chemistry*, Feb. 2009, pp. 1709-1715, vol. 17, No. 4, XP-002613422.

Parnetti, L. at al. "Vascular Dementia Italian Sulodexide Study (VA.D.I.S.S.) Clinical and Biological Results" *Thrombosis Research*, pp. 225-233, vol. 87, No. 2.

Polizopoulou, Z. S. at al. "Evaluation of a Proposed Therapeutic Protocol in 12 Dogs with Tentative Degenerative Myelopathy" *Act Veterinaria Hungarica*, pp. 293-301, Sep. 2008, vol. 56, No. 56, No. 3, XP-009142152.

Pooler, A. M. at al. "The 3-hydroxy-3-methylglutaryl co-enzyme A reductase inhibitor pravastatin enhances neurite outgrowth in hippocampal neurons" *Journal of Neurochemistry*, May 2006, pp. 716-723, vol. 97, No. 3, XP-002571001.

Roehl, A. B. et al. "Neuroprotective properties of levosimendan in an in vitro model of traumatic brain injury" *BMC Neurology*, Oct. 21, 2010, pp. 1-4, vol. 10, No. 1, XP-021074880.

Spuch, C. at al, "Induction of angiogenesis by implantation of encapsulated cells expressing vegf: A new therapy approach on Alzheimer's disease?" *Journal of Neurological Sciences*, Aug. 2009, p. 260, vol. 283, No. 1-2, Issue 1, XP-002571001.

Van Den Bussche, H. et al. "Prescription patterns and effectiveness perception of anti-dementia drugs- A comparison between General Practitioners, Neurologists and Psychiatrists" *Nervenheilkunde*, 2005, pp. 485-492, vol. 24, No. 6, XP-009144765.

Wang, B. et al. "Protective Effects of Wu-Zi-Yan-Zong-Fang on Amyloid β-induced Damage In Vitro and In Vitro" *Database Biosis* [Online] *Biosciences Information Service*, Aug. 2009, pp. 941-948, vol. 129, No. 8.

Yoshida, K. et al. "Eplernone Enhances Neovascularization Induced by Endothelial Progenitor Cells in Rat Hindlimb Ischemia" *18th Scientific Meeting of the European-Society-of-Hypertension*, 22nd Scientific Meeting of the Inter, Berlin, Germany, Jun. 14-19, 2008, Poster session Pj-413, XP-009144604, abstract only.

Database Blosis [Online] Bioscience Information Service, Philadelphia, PA, Yoshihiko K. et al., "Donepezil, in acetylcholisteras inhibitor against Alzheimer's dementia, promotes angiogenesis in an ischemic limb model of nicotinic alpha 7 k0 mice" Database Accession No. PREV200800197710, Oct. 2007, pp. 1-2, vol. 116, No. 16, Suppl. S., XP-002613420.

Database Biosis [Online] Bioscience Information Service, Philadelphia, PA, Wang, B. et al. "Protective Effects of Wu-Zi-Yan-Zong-Fang on Amyloid β-induced Damage In Vivo and In Vitro" Database Accession No. PREV200900521928, Aug. 2009, pp. 1-2, vol. 129, No. 8, Suppl. S., XP-002613420.

Berenbaum, M.C., "Synergy, additivism and antagonism in immunosuppression: A Critical Review," *Clin. exp. Immunol.*, 1977, pp. 1-18, vol. 28.

Jalbert, J.J. et al., "Dementia of the Alzheimer Type," *Epidemiologic Reviews*, 2008, pp. 15-34, vol. 30.

Jantzen and Robinson, *Modern Pharaceutics 3rd Edition*, published 1996, Marcel Dekker Inc., New York, NY, ed. Gilbert S. Banker et al., p. 596.

Levin, E.D. et al., "Baclofen interactions with nicotine in rats: effects on memory," *Pharmacology, Biochemistry and Behavior*, 2004, pp. 343-348, vol. 79.

Rogers, S.L. et al., "Donepezil Improves Cognition and Global Function in Alzheimer Disease," *Arch Intern Med*, 1998, pp. 1021-1031, vol. 158.

Rosse, R.B. et al., "Baclofen Treatment in a Patient With Tardive Dystonia," *J. Clin Psychiatry*, 1986, pp. 474-475, vol. 47.

Wilcox, D.M. et al., "Anti-Aβ immunotherapy in Alzheimer's disease; relevance of transgenic mouse studies to clinical trials," *J. Alzheimers Dis.*, 2008, pp. 555-569, vol. 15, No. 4.

\* cited by examiner

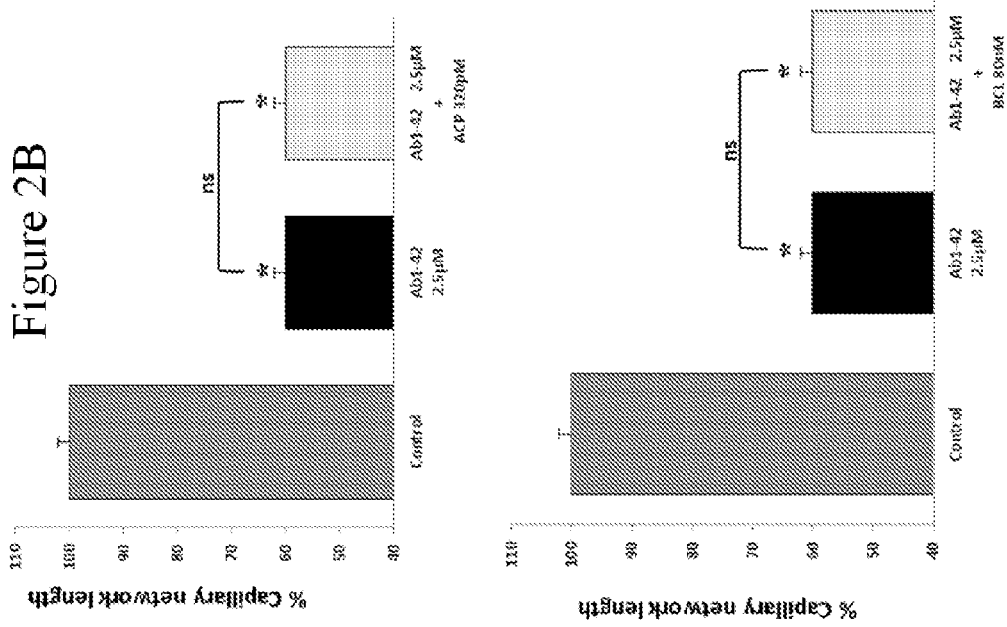
Figure 2B
Figure 2C
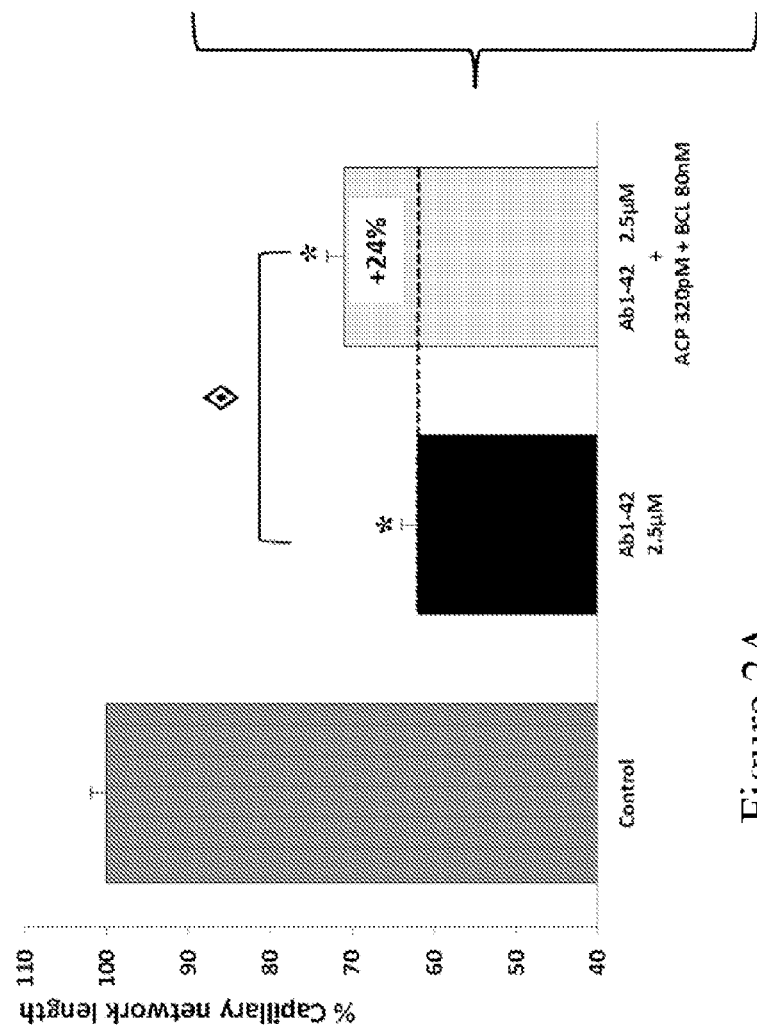
Figure 2A

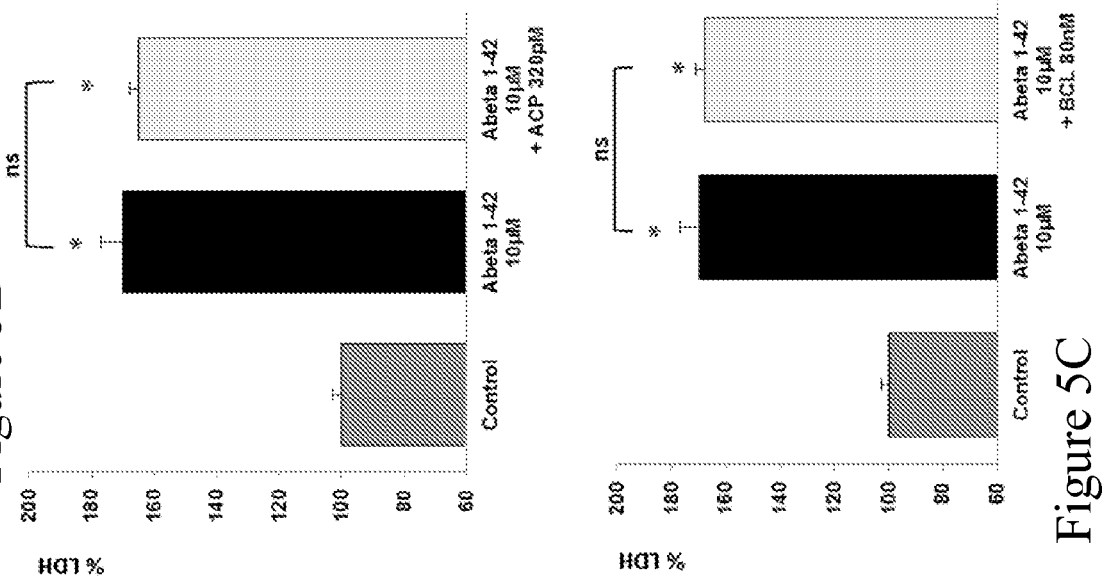
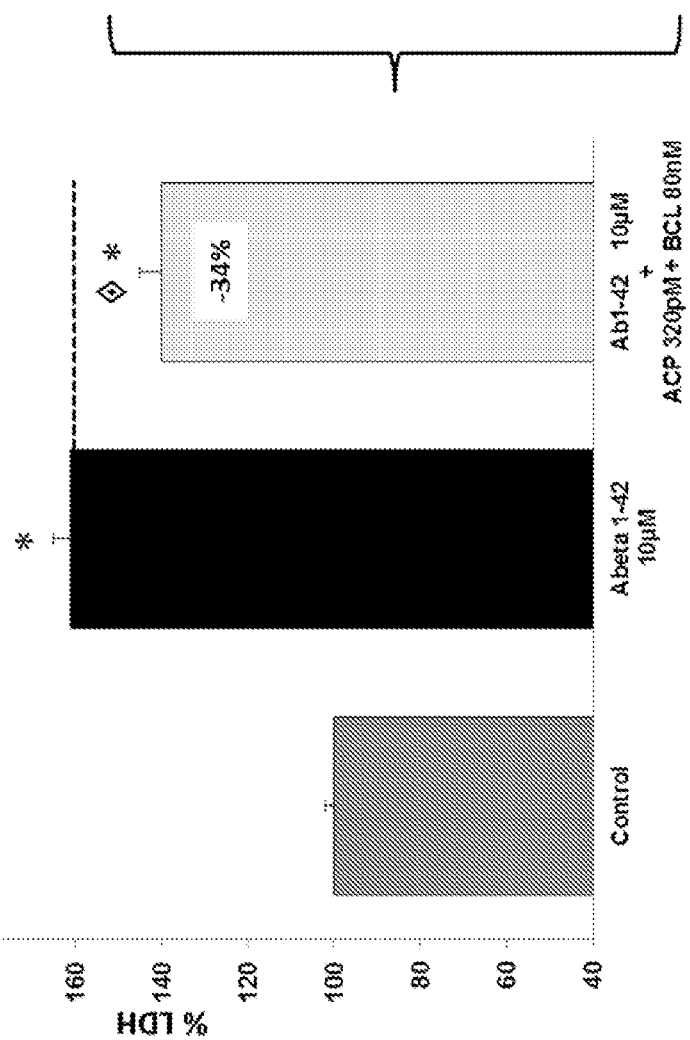
Figure 5B
Figure 5C
Figure 5A

SEQUENCE LISTING

```
<160> NUMBER OF SEQ ID NOS: 1

<210> SEQ ID NO 1
<211> LENGTH: 21
<212> TYPE: PRT
<213> ORGANISM: Artificial sequence
<220> FEATURE:
<223> OTHER INFORMATION: myelin-oligodendrocyte glycoprotein

<400> SEQUENCE: 1
```

```
-continued

Met Glu Val Gly Trp Tyr Arg Ser Pro Phe Ser Arg Val Val His Leu
1               5               10                  15

Tyr Arg Asn Gly Lys
            20
```

BACLOFEN AND ACAMPROSATE BASED THERAPY OF NEUROLOGICAL DISORDERS

FIELD OF THE INVENTION

The present invention relates to combinations and methods for the treatment of neurological diseases and disorders. More specifically, the present invention relates to novel combinatorial therapy of neurological disorders, based on Baclofen and Acamprosate combination.

BACKGROUND OF THE INVENTION

Alzheimer's disease (AD) is the prototypic cortical dementia characterized by memory deficit together with dysphasia (language disorder in which there is an impairment of speech and of comprehension of speech), dyspraxia (disability to coordinate and perform certain purposeful movements and gestures in the absence of motor or sensory impairments) and agnosia (ability to recognize objects, persons, sounds, shapes, or smells) attributable to involvement of the cortical association areas. Special symptoms such as spastic paraparesis (weakness affecting the lower extremities) can also be involved (1-4).

Incidence of Alzheimer disease increases dramatically with the age. AD is at present the most common cause of dementia. It is clinically characterized by a global decline of cognitive function that progresses slowly and leaves end-stage patients bound to bed, incontinent and dependent on custodial care. Death occurs, on average, 9 years after diagnosis (5).

The incidence rate of AD increases dramatically with age. United Nation population projections estimate that the number of people older than 80 years will approach 370 million by the year 2050. Currently, it is estimated that 50% of people older than age 85 years are afflicted with AD. Therefore, more than 100 million people worldwide will suffer from dementia in 50 years. The vast number of people requiring constant care and other services will severely affect medical, monetary and human resources (6).

Memory impairment is the early feature of the disease and involves episodic memory (memory for day-today events). Semantic memory (memory for verbal and visual meaning) is involved later in the disease. By contrast, working memory (short-term memory involving structures and processes used for temporarily storing and manipulating information) and procedural memory (unconscious memory that is long-term memory of skills and procedure) are preserved until late. As the disease progresses, the additional features of language impairment, visual perceptual and spatial deficits, agnosias and apraxias emerge.

The classic picture of Alzheimer's disease is sufficiently characteristic to allow identification in approximately 80% of cases (7). Nevertheless, clinical heterogeneity does occur and not only is this important for clinical management but provides further implication of specific medication treatments for functionally different forms (8).

The pathological hallmark of AD includes amyloid plaques containing beta-amyloid (Abeta), neurofibrillary tangles (NFT) containing Tau and neuronal and synaptic dysfunction and loss (9-11). For the last decade, two major hypotheses on the cause of AD have been proposed: the "amyloid cascade hypothesis", which states that the neurodegenerative process is a series of events triggered by the abnormal processing of the Amyloid Precursor Protein (APP) (12), and the "neuronal cytoskeletal degeneration hypothesis" (13), which proposes that cytoskeletal changes are the triggering events. The most widely accepted theory explaining AD progression remains the amyloid cascade hypothesis (14-16) and AD researchers have mainly focused on determining the mechanisms underlying the toxicity associated with Abeta proteins. Microvascular permeability and remodeling, aberrant angiogenesis and blood brain barrier breakdown have been identified as key events contributing to the APP toxicity in the amyloid cascade (17). On contrary, Tau protein has received much less attention from the pharmaceutical industry than amyloid, because of both fundamental and practical concerns. Moreover, synaptic density change is the pathological lesion that best correlates with cognitive impairment than the two others. Studies have revealed that the amyloid pathology appears to progress in a neurotransmitter-specific manner where the cholinergic terminals appear most vulnerable, followed by the glutamatergic terminals and finally by the GABAergic terminals (11). Glutamate is the most abundant excitatory neurotransmitter in the mammalian nervous system. Under pathological conditions, its abnormal accumulation in the synaptic cleft leads to glutamate receptors overactivation (18). Abnormal accumulation of glutamate in synaptic cleft leads to the overactivation of glutamate receptors that results in pathological processes and finally in neuronal cell death. This process, named excitotoxicity, is commonly observed in neuronal tissues during acute and chronic neurological disorders.

It is becoming evident that excitotoxicity is involved in the pathogenesis of multiple disorders of various etiology such as: spinal cord injury, stroke, traumatic brain injury, hearing loss, alcoholism and alcohol withdrawal, alcoholic neuropathy, or neuropathic pain as well as neurodegenerative diseases such as multiple sclerosis, Alzheimer's disease, Amyotrophic Lateral Sclerosis, Parkinson's disease, and Huntington's disease (19-21). The development of efficient treatment for these diseases remains major public health issues due to their incidence as well as lack of curative treatments.

Two kinds of medication are used for improving or slowing down symptoms of AD which lay on some acetylcholinesterase modulators and blockers of NMDA glutamate receptors (26-27).

NMDAR antagonists that target various sites of this receptor have been tested to counteract excitotoxicity. Uncompetitive NMDAR antagonists target the ion channel pore thus reducing the calcium entry into postsynaptic neurons. Some of them reached the approval status. As an example, Memantine is currently approved in moderate to severe Alzheimer's disease. It is clinically tested in other indications that include a component of excitotoxicity such as alcohol dependence (phase II), amyotrophic lateral sclerosis (phase III), dementia associated with Parkinson (Phase II), epilepsy, Huntington's disease (phase IV), multiple sclerosis (phase IV), Parkinson's disease (phase IV) and traumatic brain injury (phase IV). This molecule is however of limited benefit to most Alzheimer's disease patients, because it has only modest symptomatic effects. Another approach in limiting excitotoxicity consists in inhibiting the presynaptic release of glutamate. Riluzole, currently approved in amyotrophic lateral sclerosis, showed encouraging results in ischemia and traumatic brain injury models (22-25). It is at present tested in phase II trials in early multiple sclerosis, Parkinson's disease (does not show any better results than placebo) as well as spinal cord injury. In 1995, the drug reached orphan drug status for the treatment of amyotrophic lateral sclerosis and in 1996 for the treatment of Huntington's disease. The use of NMDA receptor antagonists such as memantine, felbamate, acamprosate and MRZ 2/579 for treating depression has also been suggested in US2010076075.

WO2009133128, WO2009133141, WO2009133142 and WO2011054759 disclose drug combinations for use in the treatment of AD.

Despite active research in this area, there is still a need for alternative or improved efficient therapies for neurological disorders and, in particular, neurological disorders which are related to glutamate and/or amyloid beta toxicity. The present invention provides new treatments for such neurological diseases of the central nervous system (CNS) and the peripheral nervous system (PNS).

SUMMARY OF INVENTION

It is an object of the present invention to provide new therapeutic methods and compositions for treating neurological disorders. More particularly, the invention relates to compositions and methods for treating neurological disorders related to glutamate and/or amyloid beta toxicity, based on a combination of Baclofen and Acamprosate.

The invention stems, inter alia, from the unexpected discovery, by the inventors, that the combination of Baclofen and Acamprosate provides substantial and unexpected benefit to patients with Alzheimer's disease. Moreover, the inventors have surprisingly discovered that this combination provides substantial and unexpected protection of neuronal cells against various injuries encountered in neurological disorders including glutamate toxicity. Thus, this combination of Baclofen and Acamprosate constitutes an efficient treatment for patients suffering from, predisposed to, or suspected to suffer from neurological disorders.

An object of this invention therefore relates to compositions comprising a combination Baclofen and Acamprosate, for use in the treatment of a neurological disorder, particularly AD and related disorders, Multiple Sclerosis (MS), Amyotrophic Lateral Sclerosis (ALS), Parkinson's disease (PD), neuropathies (for instance neuropathic pain or alcoholic neuropathy), alcoholism or alcohol withdrawal, Huntington's disease (HD) and spinal cord injury.

The composition of the invention may contain Baclofen and Acamprosate as the only active ingredients. Alternatively, the compositions may comprise additional active ingredient(s). In this regard, a further object of this invention relates to a composition comprising a combination of Baclofen, Acamprosate, and at least one third compound selected from Sulfisoxazole, Methimazole, Prilocaine, Dyphylline, Quinacrine, Carbenoxolone, Aminocaproic acid, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Ifenprodil, Moxifloxacin, Bromocriptine or Torasemide, for use in the treatment of neurological disorders in a subject in need thereof.

As it will be further disclosed in the present application, the compounds in a combinatorial therapy of the invention may be administered simultaneously, separately, sequentially and/or repeatedly to the subject.

The invention also relates to any pharmaceutical composition per se comprising a combination of at least two compounds as defined above.

The compositions of the invention typically further comprise one or several pharmaceutically acceptable excipients or carriers. Also, the compounds as used in the present invention may be in the form of a salt, hydrate, ester, ether, acid, amide, racemate, or isomer. They may also be in the form of sustained-release formulations. Prodrugs or derivatives of the compounds may be used as well.

In a preferred embodiment, the compound is used as such or in the form a salt, hydrate, ester, ether or sustained release form thereof. A particularly preferred salt for use in the present invention is Acamprosate calcium.

In another preferred embodiment, a prodrug or derivative is used.

A further object of this invention is a method of preparing a pharmaceutical composition, the method comprising mixing Baclofen and Acamprosate, in a pharmaceutically acceptable excipient or carrier.

Another object of this invention relates to a method for treating a neurological disorder in a mammalian subject in need thereof, preferably a human subject in need thereof, the method comprising administering to said subject an effective amount of a combination of the invention.

A further object of this invention relates to a method for treating Alzheimer or a related disorder in a mammalian subject in need thereof, preferably a human subject in need thereof, the method comprising administering to said subject an effective amount of a combination of the invention.

A preferred object of this invention relates to a method for treating a neurological disorder in a mammalian subject in need thereof, preferably a human subject in need thereof, the method comprising simultaneously, separately or sequentially administering to said subject an effective amount of Baclofen and Acamprosate.

A more preferred object of this invention relates to a method for treating Alzheimer or a related disorder in a mammalian subject in need thereof, preferably a human subject in need thereof, the method comprising simultaneously, separately or sequentially administering to said subject an effective amount of Baclofen and Acamprosate.

The invention may be used for treating a neurological disorder in any mammalian subject, preferably in any human subject, at any stage of the disease. As will be disclosed in the examples, the compositions of the invention are able to ameliorate the pathological condition of said subjects.

BRIEF DESCRIPTION OF THE FIGURES

FIG. 2: Effect of Baclofen (BCL) and Acamprosate (ACP) combination therapy on the total length of capillary network in beta-amyloid intoxicated HBMEC cultures. The human amyloid peptide ($A\beta_{1-42}$ 2.5 µM) produces a significant intoxication, above 40%, compared to vehicle-treated cells. This intoxication is significantly prevented by the combination of Acamprosate and Baclofen (A) whereas, at those concentrations, Acamprosate (B) and Baclofen (C) alone have no significant effect on intoxication. ◊: $p<0.05$, significantly different from $A\beta_{1-42}$ intoxication; *: $p<0.05$, significantly different from vehicle; "ns" no significant effect (ANOVA+Dunnett Post-Hoc test).

FIG. 5: Effect of Acamprosate (ACP) and Baclofen (BCL) combination therapy on LDH release in human $A\beta_{1-42}$ toxicity on rat primary cortical cells. The human amyloid peptide ($A\beta_{1-42}$ 10 μM) produces a significant intoxication compared to vehicle-treated neurons. This intoxication is significantly prevented by the combination of Acamprosate and Baclofen (A) whereas, at those concentrations, Acamprosate (B) and Baclofen (C) alone have no significant effect on intoxication. ◊: p<0.05, significantly different from $A\beta_{1-42}$ intoxication; *: p<0.05, significantly different from vehicle; "ns" no significant effect. (ANOVA+Dunnett Post-Hoc test).

DETAILED DESCRIPTION OF THE INVENTION

Figure 1:
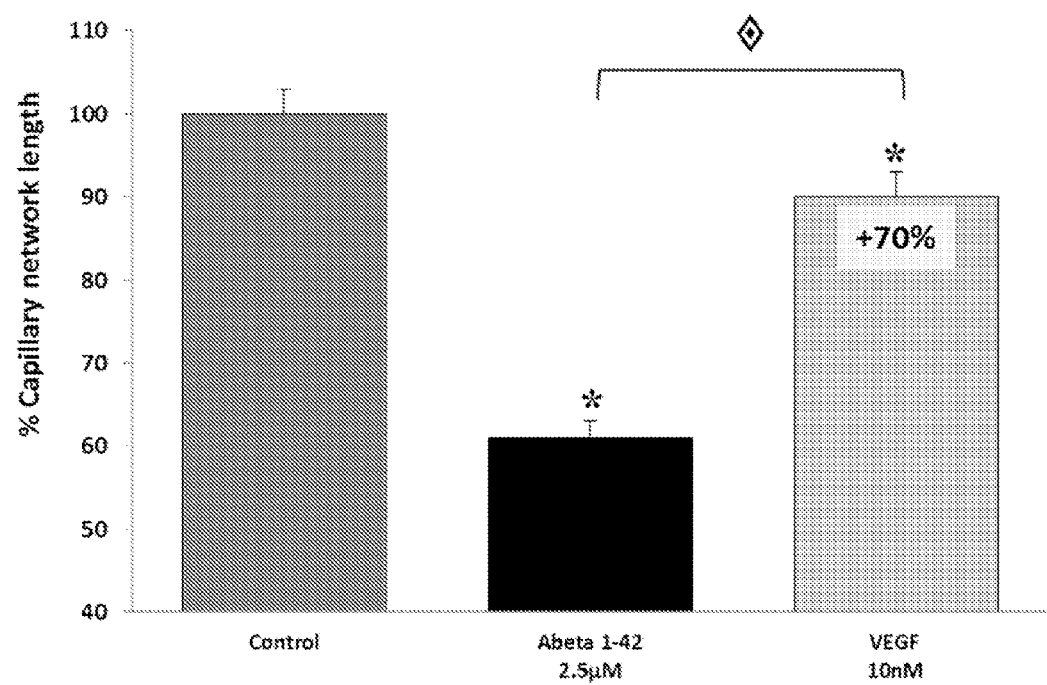
FIG. 1: Validation of the experimental model of human βamyloid's toxicity on endothelial cells used for drug screening. One hour of VEGF pre-treatment at 10 nM significantly protected the capillary network from this amyloid injury (+70% of capillary network compared to amyloid intoxication).

The present invention provides new methods and compositions for treating neurological disorders. The invention discloses novel drug combinations which allow an effective correction of such diseases and may be used in any mammalian subject.

The invention is suited for treating any neurological disorders, whether central or peripheral, particularly disorders wherein nerves or neurons injuries, βamyloid, BBB breakdown or glutamate excitotoxicity are involved. Specific examples of such disorders include neurodegenerative diseases, neuropathies, spinal cord injury, and substances abuse such as alcoholism.

Neurodegenerative disorders refer to diseases, such as Alzheimer's and related disorders, Amyotrophic Lateral Sclerosis (ALS), Multiple Sclerosis (MS), Parkinson's Disease (PD), Huntington's Disease (HD), encompassing a progressive loss of function and death of neurons.

Neuropathies refer to conditions where nerves of the peripheral nervous system are damaged, this include damages of the peripheral nervous system provoked by genetic factors, inflammatory disease, or by chemical substance including drugs (vincristine, oxaliplatin, ethyl alcohol). The treatment of neuropathies also includes the treatment of neuropathic pain.

The invention is particularly suited for treating AD and related disorders. In the context of this invention, the term "related disorder" includes senile dementia of AD type (SDAT), Lewis body dementia, vascular dementia, mild cognitive impairment (MCI) and age-associated memory impairment (AAMI).

As used herein, "treatment" includes the therapy, prevention, prophylaxis, retardation or reduction of symptoms provoked by or of the causes of the above diseases or disorders. The term treatment includes in particular the control of disease progression and associated symptoms. The term treatment particularly includes a protection against the toxicity caused by Amyloid Beta, or a reduction or retardation of said toxicity, and/or ii) a protection against glutamate excitotoxicity, or a reduction or retardation of said toxicity, in the treated subjects. The term treatment also designates an improvement of cognitive symptom or a protection of neuronal cells.

Within the context of this invention, the designation of a specific drug or compound is meant to include not only the specifically named molecule, but also any pharmaceutically acceptable salt, hydrate, derivative, isomer, racemate, conjugate, prodrug or derivative thereof of any chemical purity.

The term "combination or combinatorial treating/therapy" designates a treatment wherein at least Baclofen and Acamprosate are co-administered to a subject to cause a biological effect. In a combined therapy according to this invention, the at least two drugs may be administered together or separately, at the same time or sequentially. Also, the at least Baclofen and Acamprosate may be administered through different routes and protocols. As a result, although they may be formulated together, the drugs of a combination may also be formulated separately.

The term "prodrug" as used herein refers to any functional derivatives (or precursors) of a compound of the present invention, which, when administered to a biological system, generates said compound as a result of e.g., spontaneous chemical reaction(s), enzyme catalysed chemical reaction(s), and/or metabolic chemical reaction(s). Prodrugs are usually inactive or less active than the resulting drug and can be used, for example, to improve the physicochemical properties of the drug, to target the drug to a specific tissue, to improve the pharmacokinetic and pharmacodynamic properties of the drug and/or to reduce undesirable side effects. Some of the common functional groups that are amenable to prodrug design include, but are not limited to, carboxylic, hydroxyl, amine, phosphate/phosphonate and carbonyl groups. Prodrugs typically produced via the modification of these groups include, but are not limited to, esters, carbonates, carbamates, amides and phosphates. Specific technical guidance for the selection of suitable prodrugs is general common knowledge (29-33). Furthermore, the preparation of prodrugs may be performed by conventional methods known by those skilled in the art. Methods which can be used to synthesize other prodrugs are described in numerous reviews on the subject (30; 34-40). For example, Arbaclofen Placarbil is listed in ChemID plus Advance database (website: chem.sis.nlm.nih.gov/chemidplus/) and Arbaclofen Placarbil is a well-known prodrug of Baclofen (41-42).

The term "derivative" of a compound includes any molecule that is functionally and/or structurally related to said compound, such as an acid, amide, ester, ether, acetylated variant, hydroxylated variant, or an alkylated (C1-C6) variant of such a compound. The term derivative also includes structurally related compound having lost one or more substituent as listed above. For example, Homotaurine is a deacetylated derivative of Acamprosate. Preferred derivatives of a compound are molecules having a substantial degree of similarity to said compound, as determined by known methods. Similar compounds along with their index of similarity to a parent molecule can be found in numerous databases such as Pub-Chem (http://pubchem.ncbi.nlm.nih.gov/search/) or Drug-Bank (See Worldwide Website: http://www.drugbank.ca/). In a more preferred embodiment, derivatives should have a Tanimoto similarity index greater than 0.4, preferably greater than 0.5, more preferably greater than 0.6, even more preferably greater than 0.7 with a parent drug. The Tanimoto similarity index is widely used to measure the degree of structural similarity between two molecules. Tanimoto similarity index can be computed by software such as the Small Molecule Subgraph Detector (43-44) available online (See Worldwide Website: http://www.ebi.ac.uk/thornton-srv/software/SMSD/). Preferred derivatives should be both structurally and functionally related to a parent compound, i.e., they should also retain at least part of the activity of the parent drug, more preferably they should have a protective activity against Aβ or glutamate toxicity.

The term derivatives also include metabolites of a drug, e.g., a molecule which results from the (biochemical) modification(s) or processing of said drug after administration to an organism, usually through specialized enzymatic systems, and which displays or retains a biological activity of the drug. Metabolites have been disclosed as being responsible for much of the therapeutic action of the parent drug. In a specific embodiment, a "metabolite" as used herein designates a modified or processed drug that retains at least part of the activity of the parent drug; preferably that has a protective activity against Aβ toxicity or glutamate toxicity.

The term "salt" refers to a pharmaceutically acceptable and relatively non-toxic, inorganic or organic acid addition salt of a compound of the present invention. Pharmaceutical salt formation consists in pairing an acidic, basic or zwitterionic drug molecule with a counterion to create a salt version of the drug. A wide variety of chemical species can be used in neutralization reaction. Pharmaceutically acceptable salts of the invention thus include those obtained by reacting the main compound, functioning as a base, with an inorganic or organic acid to form a salt, for example, salts of acetic acid, nitric acid, tartric acid, hydrochloric acid, sulfuric acid, phosphoric acid, methane sulfonic acid, camphor sulfonic acid, oxalic acid, maleic acid, succinic acid or citric acid. Pharmaceutically acceptable salts of the invention also include those in which the main compound functions as an acid and is reacted with an appropriate base to form, e.g., sodium, potassium, calcium, magnesium, ammonium, or choline salts. Though most of salts of a given active principle are bioequivalents, some may have, among others, increased solubility or bioavailability properties. Salt selection is now a common standard operation in the process of drug development as taught by H. Stahl and C. G Wermuth in their handbook (45).

In a preferred embodiment, the designation of a compound is meant to designate the compound per se, as well as any pharmaceutically acceptable salt, hydrate, isomer, racemate, ester or ether thereof.

In a more preferred embodiment, the designation of a compound is meant to designate the compound as specifically designated per se, as well as any pharmaceutically acceptable salt thereof.

In a particular embodiment, a sustained-release formulation of the compound is used.

As discussed above, the invention relates to particular drug combinations which have a strong unexpected effect on several biological processes involved in neurological disorders. These drug combinations therefore represent novel approaches for treating neurological disorders, such as Alzheimer's disease and related disorders, Multiple Sclerosis, Amyotrophic Lateral Sclerosis, Parkinson's disease, Huntington's Disease, neuropathies (for instance neuropathic pain or alcoholic neuropathy), alcoholism or alcohol withdrawal, and spinal cord injury. More specifically, the invention discloses compositions, comprising Baclofen in combination with Acamprosate, which provide a significant effect in vivo on neurological disorders.

Indeed, the invention shows, in the experimental part, that combination therapies comprising Baclofen and Acamprosate can substantially improve the condition of patients afflicted with neurological disorders. In particular, the inventors have surprisingly discovered that Baclofen and Acamprosate combinations have a strong, unexpected effect on the length of capillary network or LDH release in beta-amyloid intoxicated nervous cells, and represent new therapeutic approaches of AD. Also, the examples show that, in a combination therapy of the invention, Baclofen may be effective at a dose of 80 nM or less, and that Acamprosate may be effective at a dose of 1 nM or less. These results are remarkable and particularly advantageous since, at such low doses, any possible side effects are avoided.

Furthermore, these combinations effectively protect neuronal cells from various afflictions such as glutamate toxicity, oxidative stress and prevent BBB permeabilization or neuronal cells induced apoptosis which are involved in several neurological disorders.

The present invention therefore proposes a novel therapy of neurological disorders, based on Baclofen and Acamprosate compositions. More particularly, the present invention therefore proposes a novel therapy of Alzheimer's disease and related disorders, Multiple Sclerosis, Amyotrophic Lateral Sclerosis, Parkinson's Disease, Huntington's Disease, neuropathies (for instance neuropathic pain or alcoholic neuropathy), alcoholism or alcohol withdrawal, and spinal cord injury, based on Baclofen and Acamprosate combinations.

In this regard, in a particular embodiment, the invention relates to a composition comprising Baclofen and Acamprosate.

In a further embodiment, the invention relates to a composition comprising Baclofen and Acamprosate for use in the treatment of AD, AD related disorders, MS, PD, ALS, HD, neuropathies (for instance neuropathic pain or alcoholic neuropathy), alcoholism or alcohol withdrawal, or spinal cord injury.

In a further embodiment, the invention relates to the use of Baclofen and Acamprosate for the manufacture of a medicament for the treatment of AD, AD related disorders, MS, PD, ALS, HD, neuropathies (for instance neuropathic pain or alcoholic neuropathy), alcoholism or alcohol withdrawal, or spinal cord injury.

Illustrative CAS numbers for Baclofen and Acamprosate are provided in Table 1 below. Table 1 cites also, in a non-limitative way, common salts, racemates, prodrugs, metabolites or derivatives for these compounds used in the compositions of the invention.

TABLE 1

| Drug | CAS Numbers | Class or Tanimoto similarity index |
|---|---|---|
| Acamprosate and related compounds | | |
| Acamprosate | 77337-76-9; 77337-73-6 | NA |
| Homotaurine | 3687-18-1 | 0.73 |
| Ethyl Dimethyl Ammonio Propane Sulfonate | / | 0.77 |
| Taurine | 107-35-7 | 0.5 |
| Baclofen and related compounds | | |
| Baclofen | 1134-47-0; 66514-99-6; 69308-37-8; 70206-22-3; 63701-56-4; 63701-55-3 | NA |
| 3-(p-chlorophenyl)-4-hydroxybutyric acid | / | Metabolite |
| Arbaclofen placarbil | 847353-30-4 | Prodrug |

Specific examples of prodrugs of Baclofen are given in Hanafi et al., 2011 (41), particularly Baclofen esters and Baclofen ester carbamates, which are of particular interest for CNS targeting. Hence such prodrugs are particularly suitable for compositions of this invention. Baclofen placarbil as mentioned before is also a well-known prodrug and may thus be used instead of Baclofen in compositions of the invention. Other prodrugs of Baclofen can be found in the following patent applications: WO2010102071, US2009197958, WO2009096985, WO2009061934, WO2008086492, US2009216037, WO2005066122, US2011021571, WO2003077902, and WO2010120370.

Useful prodrugs for acamprosate such as pantoic acid ester neopentyl sulfonyl esters, neopentyl sulfonyl esters prodrugs or masked carboxylate neopentyl sulfonyl ester prodrugs of acamprosate are notably listed in WO2009033069, WO2009033061, WO2009033054 WO2009052191, WO2009033079, US 2009/0099253, US 2009/0069419, US 2009/0082464, US 2009/0082440, and US 2009/0076147.

Baclofen and Acamprosate may be used alone or may be further combined with additional compounds. In this regard, in a particular embodiment, the compositions of the invention may further comprise at least one compound selected from Sulfisoxazole, Methimazole, Prilocaine, Dyphylline, Quinacrine, Carbenoxolone, Aminocaproic acid, Cabergoline, Diethylcarbamazine, Cinacalcet, Cinnarizine, Eplerenone, Fenoldopam, Leflunomide, Levosimendan, Sulodexide, Terbinafine, Zonisamide, Etomidate, Phenformin, Trimetazidine, Mexiletine, Ifenprodil, Moxifloxacin, Bromocriptine or Torasemide. Illustrative CAS numbers for each of these compounds are provided in Table 2 below:

TABLE 2

| DRUG NAME | CAS NUMBER |
| --- | --- |
| Aminocaproic Acid | 60-32-2 |
| Bromocriptine | 25614-03-3 |
| Cabergoline | 81409-90-7 |
| Carbenoxolone | 5697-56-3 |
| Cinacalcet | 226256-56-0 |
| Cinnarizine | 298-57-7 |
| Diethylcarbamazine | 90-89-1 |
| Dyphylline | 479-18-5 |
| Eplerenone | 107724-20-9 |
| Etomidate | 33125-97-2 |
| Fenoldopam | 67227-57-0 |
| Ifenprodil | 23210-56-2 or 23210-58-4 |
| Leflunomide | 75706-12-6 |
| Levosimendan | 141505-33-1 |
| Methimazole | 60-56-0 |
| Mexiletine | 5370-01-4 or 31828-71-4 |
| Moxifloxacin | 354812-41-2 |
| Phenformin | 114-86-3 |
| Prilocaine | 721-50-6 or 14289-31-7 or 14289-32-8 |
| Quinacrine | 83-89-6 |
| Sulfisoxazole | 127-69-5 |
| Sulodexide | 57821-29-1 |
| Terbinafine | 91161-71-6 |
| Torasemide | 56211-40-6 or 72810-59-4 |
| Trimetazidine | 5011-34-7 or 13171-25-0 |
| Zonisamide | 68291-97-4 |

In a particular embodiment, the invention relates to the use of this combination for treating AD or a related disorder in a subject in need thereof.

In a particular embodiment, the invention relates to the use of this combination for treating MS, PD, ALS, HD, neuropathies (for instance neuropathic pain or alcoholic neuropathy), alcoholism or alcohol withdrawal, or spinal cord injury, in a subject in need thereof.

As disclosed in the examples, composition therapies using at least Baclofen and Acamprosate have a strong unexpected effect on biological processes leading to neuronal injuries. Furthermore, these combinations also showed in vivo a very efficient ability to correct symptoms of neurological diseases. These combinations therefore represent novel approaches for treating neurological disorders, such as Alzheimer's disease, Multiple Sclerosis, Amyotrophic Lateral Sclerosis, Parkinson's Disease, Huntington's Disease, neuropathies (for instance neuropathic pain or alcoholic neuropathy), alcoholism or alcohol withdrawal, and spinal cord injury. These compositions efficiently prevent toxicity of amyloid β (Aβ) peptide or glutamate excitotoxicity on neuronal cells. Moreover, in vivo, these compositions lead to an improvement of several cognitive symptoms as well as to a protection of neuronal cells. Hence they represent novel and potent methods for treating such disorders.

The experimental section further shows that the above mentioned compositions are also efficient i) in synergistically protecting in vitro neuronal cells from glutamate excitotoxicity, and ii) in conferring clinical benefit in in vivo models for diseases related to glutamate excitotoxicity.

The compositions of the invention may comprise 2, 3, 4 or 5 distinct drugs, more preferably 2, 3 or 4 distinct drugs for combinatorial treatment of Alzheimer's disease (AD), AD related disorders, MS, PD, ALS, HD, neuropathies (for instance neuropathic pain or alcoholic neuropathy), alcoholism or alcohol withdrawal, or spinal cord injury in a subject in need thereof. In a preferred embodiment, the drugs of the invention are used in combination(s) for combined, separate or sequential administration, in order to provide the most effective effect.

Preferred compositions of the invention, for use in the treatment of a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, comprise one of the following drug combinations, for combined, separate or sequential administration:

Baclofen and Acamprosate,
Baclofen and Acamprosate and Diethylcarbamazine,
Baclofen and Acamprosate and Cinacalcet,
Baclofen and Acamprosate and Sulfisoxazole,
Baclofen and Acamprosate and Torasemide,
Baclofen and Acamprosate and Ifenprodil,
Baclofen and Acamprosate and Mexiletine,
Baclofen and Acamprosate and Eplerenone,
Baclofen and Acamprosate and Levosimendan,
Baclofen and Acamprosate and Terbinafine, or
Baclofen and Acamprosate and Leflunomide.

As disclosed in the experimental section, combinatorial therapies of the invention provide substantial therapeutic and biological effect to improve Alzheimer's disease or related disorders in human subjects. They induce a strong neuroprotective effect against Aβ toxicity and give positive results in behavioural performances and biochemical assays in vivo. Results show that compositions of the invention i) efficiently correct molecular pathways triggered, in vivo, by Aβ aggregates and ii) lead to an improvement of neurophysiological impairments observed in diseased animals as neuron survival or synapse integrity.

Figure 15:
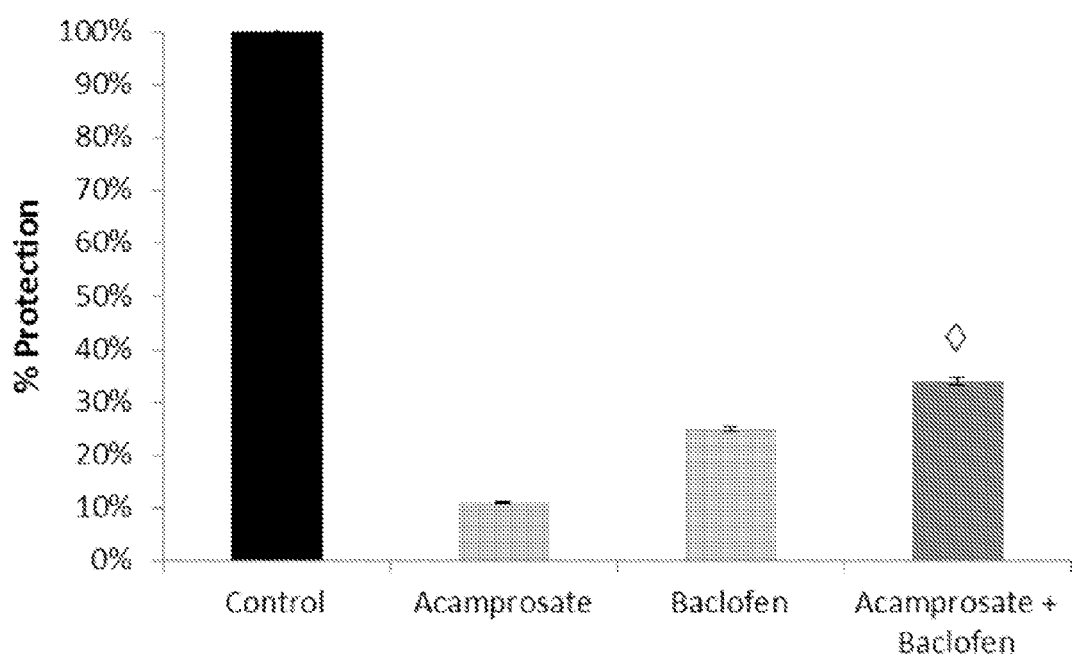
FIG. 15: Effect of Baclofen and Acamprosate combination therapy against glutamate toxicity on neuronal cortical cells Glutamate intoxication is significantly prevented by the combination of Baclofen (400 nM) and Acamprosate (1.6 nM) whereas, at those concentrations, Baclofen and Acamprosate alone have no significant effect on intoxication. ◊: p<0.001, significantly different from glutamate intoxication; (ANOVA+Dunnett Post-Hoc test).

Moreover, the results presented show also that the above combinations therapies have an important synergistic neuroprotecting effect against glutamate excitotoxicity (FIG. 15) a pathway which is implicated in various neurological diseases as AD, MS, PD, ALS, HD, neuropathies (for instance neuropathic pain or alcoholic neuropathy), alcoholism or alcohol withdrawal, or spinal cord injury. These therapies give positive results in in vivo or in vitro models for these diseases.

In addition, in vivo results show that compositions of the invention efficiently restore Brain Blood Barrier integrity and prevent, retard, or lessen apoptosis triggering, which are known to be impaired in several neurological diseases.

Furthermore, the particularly high synergisitic interaction observed for these two drugs allows the use drug concentrations showing no effect when used in single drug treatment. Moreover, as shown in the experimental section, Baclofen and Acamprosate combination causes an enhanced therapeutic benefit on Alzheimer's disease compared to other therapeutic combinations. These compositions efficiently prevent the toxic effects of amyloid β protein or peptide on human cells and in an in vivo model and represent novel and potent methods for treating such disorder.

An object of this invention thus also resides in a composition as defined above for treating a neurological disorder such as Alzheimer's disease (AD), AD related disorders, MS, PD, ALS, HD, neuropathies (for instance alcoholic neuropathy or neuropathic pain), alcoholism or alcohol withdrawal, or spinal cord injury.

As indicated previously, in a combination therapy of this invention, the compounds or drugs may be formulated together or separately, and administered together, separately or sequentially.

A further object of this invention resides in the use of a composition as defined above for the manufacture of a medicament for treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury.

The invention further provides a method for treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, comprising administering to a subject in need thereof an effective amount of a composition as disclosed above.

A further object of the invention is a method of treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury, the method comprising simultaneously, separately or sequentially administering to a subject in need thereof an effective amount of a composition as disclosed above.

In a preferred embodiment, the invention relates to a method of treating a neurological disorder such as Alzheimer's disease (AD), AD related disorders, MS, PD, ALS, HD, neuropathies (for instance neuropathic pain or alcoholic neuropathy), alcoholism or alcohol withdrawal, or spinal cord injury in a subject in need thereof, comprising administering simultaneously, separately or sequentially to the subject an effective amount of Baclofen and Acamprosate.

The compositions of the invention typically comprise one or several pharmaceutically acceptable carriers or excipients. Also, for use in the present invention, the drugs or compounds are usually mixed with pharmaceutically acceptable excipients or carriers.

In this regard, a further object of this invention is a method of preparing a pharmaceutical composition, the method comprising mixing the above compounds in an appropriate excipient or carrier.

In a particular embodiment, the method comprises mixing Baclofen and Acamprosate in an appropriate excipient or carrier.

According to preferred embodiments of the invention, as indicated above, the compounds are used as such or in the form of a pharmaceutically acceptable salt, prodrug, derivative, or sustained release formulation thereof.

Although very effective in vitro and in vivo, depending on the subject or specific condition, the combination therapy of the invention may further be used in conjunction or association or combination with additional drugs or treatments beneficial to the treated neurological condition in the subjects.

Figure 16:
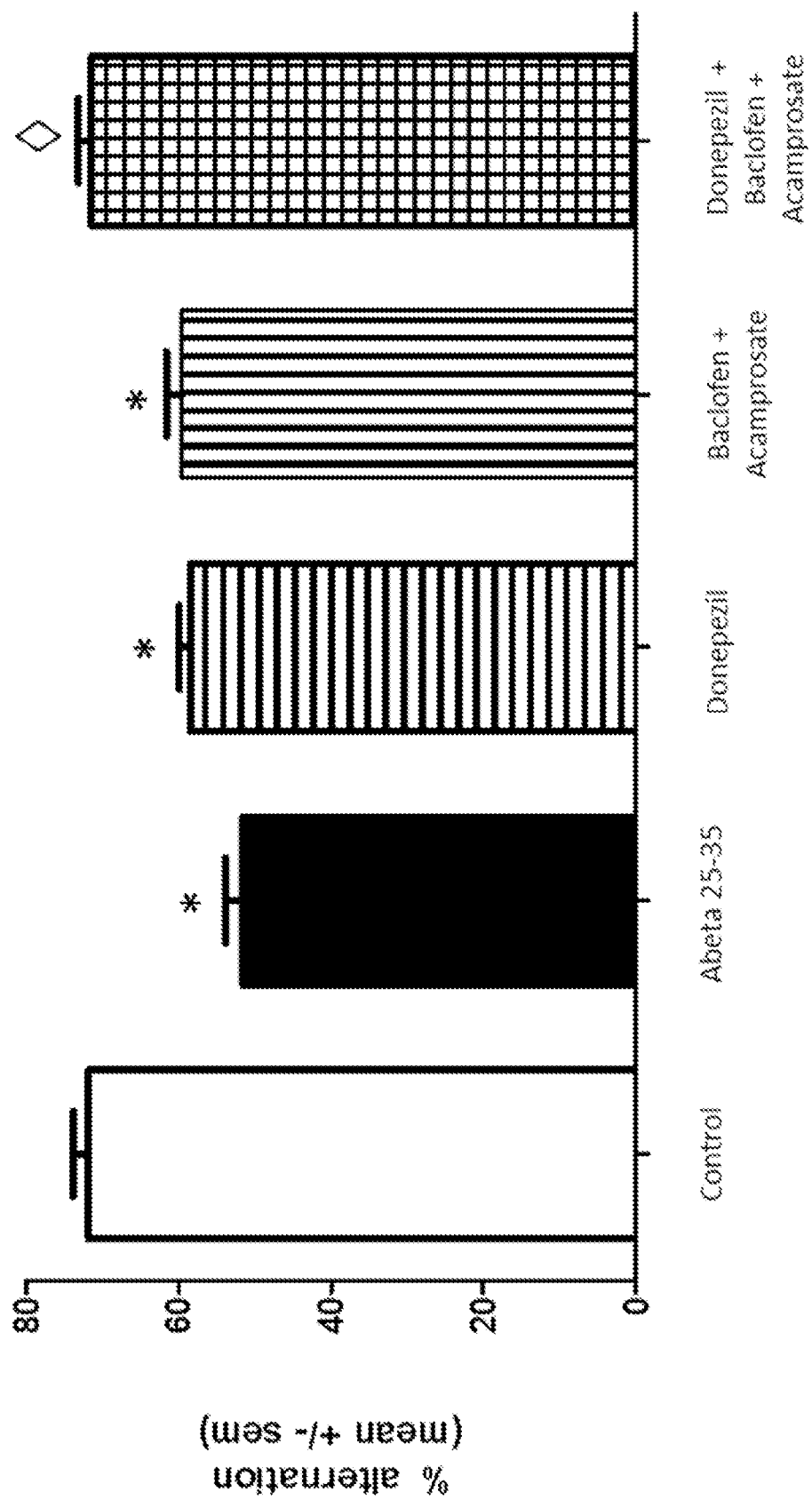
FIG. 16: Effect of Donepezil, Acamprosate and Baclofen combination therapy on behaviour and cognitive performances as defined by Y-maze test. The amyloid peptide produces a significant decrease in cognition as measured by percentage of alternation (51.5% versus 71.8%). This deleterious effect is significantly prevented (98% of protection) by the combination of Donepezil (0.25 mg/kg/day), Acamprosate (32 μg/kg/day) and Baclofen (480 μg/kg/day), whereas at those concentrations drugs alone have no significant effect. ◊: p<0.01, significantly different from $A\beta_{25-35}$ intoxication; *: p<0.01, significantly different from vehicle (ANOVA+Dunnett Post-Hoc test).

Other therapies used in conjunction with drug(s) or drug(s) combination(s) according to the present invention, may comprise one or more drug(s) that ameliorate symptoms of Alzheimer's disease, an AD related disorder, MS, PD, ALS, HD, neuropathies (for instance neuropathic pain or alcoholic neuropathy), alcoholism or alcohol withdrawal, or spinal cord injury, or drug(s) that could be used for palliative treatment of these disorders. For instance, results show also that the above combinations therapies have an important synergistic neuro-protecting effect when combined with donepezil (FIG. 16). Thereby, illustrative therapies which can be used with combinations of the invention are Donepezil (CAS: 120014-06-4), Gabapentine (CAS: 478296-72-9; 60142-96-3), Rivastigmine (123441-03-2) or Memantine (CAS: 19982-08-2).

In this regard, in a particular embodiment, the drug(s) or compositions according to the present invention may be further combined with *Ginkgo Biloba* extracts. Suitable extracts include, without limitation, *Ginkgo biloba* extracts, improved *Ginkgo biloba* extracts (for example enriched in active ingredients or lessened in contaminant) or any drug containing *Ginkgo biloba* extracts.

Therapy according to the invention may be provided at home, the doctor's office, a clinic, a hospital's outpatient department, or a hospital, so that the doctor can observe the therapy's effects closely and make any adjustments that are needed.

The duration of the therapy depends on the stage of the disease being treated, age and condition of the patient, and how the patient responds to the treatment. The dosage, frequency and mode of administration of each component of the combination can be controlled independently. For example, one drug may be administered orally while the second drug may be administered intramuscularly. Combination therapy may be given in on-and-off cycles that include rest periods so that the patient's body has a chance to recovery from any as yet unforeseen side-effects. The drugs may also be formulated together such that one administration delivers all drugs.

The administration of each drug of the combination may be by any suitable means that result in a concentration of the drug that, combined with the other component, is able to ameliorate the patient condition or efficiently treat the disease or disorder.

While it is possible for the drugs the combination to be administered as the pure chemical it is preferable to present them as a pharmaceutical composition, also referred to in this context as pharmaceutical formulation. Possible compositions include those suitable for oral, rectal, topical (including transdermal, buccal and sublingual), or parenteral (including subcutaneous, intramuscular, intravenous and intradermal) administration.

More commonly these pharmaceutical formulations are prescribed to the patient in "patient packs" containing a number dosing units or other means for administration of metered unit doses for use during a distinct treatment period in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in traditional prescriptions. The inclusion of a package insert has been shown to improve patient compliance with the physician's instructions. Thus, the invention further includes a pharmaceutical formulation, as herein before described, in combination with packaging material suitable for said formulations. In such a patient pack the intended use of a formulation for the combination treatment can be inferred by instructions, facilities, provisions, adaptations and/or other means to help using the formulation most suitably for the treatment. Such measures make a patient pack specifically suitable for and adapted for use for treatment with the combination of the present invention.

The drug may be contained, in any appropriate amount, in any suitable carrier substance. The drug may be present in an amount of up to 99% by weight of the total weight of the composition. The composition may be provided in a dosage form that is suitable for the oral, parenteral (e.g., intravenously, intramuscularly), rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols.

The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions according to the invention may be formulated to release the active drug substantially immediately upon administration or at any predetermined time or time period after administration.

The controlled release formulations include (i) formulations that create a substantially constant concentration of the drug within the body over an extended period of time; (ii) formulations that after a predetermined lag time create a substantially constant concentration of the drug within the body over an extended period of time; (iii) formulations that sustain drug action during a predetermined time period by maintaining a relatively, constant, effective drug level in the body with concomitant minimization of undesirable side effects associated with fluctuations in the plasma level of the active drug substance; (iv) formulations that localize drug action by, e.g., spatial placement of a controlled release composition adjacent to or in the diseased tissue or organ; and (v) formulations that target drug action by using carriers or chemical derivatives to deliver the drug to a particular target cell type.

Administration of drugs in the form of a controlled release formulation is especially preferred in cases in which the drug has (i) a narrow therapeutic index (i.e., the difference between the plasma concentration leading to harmful side effects or toxic reactions and the plasma concentration leading to a therapeutic effect is small; in general, the therapeutic index, TI, is defined as the ratio of median lethal dose (LD50) to median effective dose (ED50)); (ii) a narrow absorption window in the gastro-intestinal tract; or (iii) a very short biological half-life so that frequent dosing during a day is required in order to sustain the plasma level at a therapeutic level.

Any of a number of strategies can be pursued in order to obtain controlled release in which the rate of release outweighs the rate of metabolism of the drug in question. Controlled release may be obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner (single or multiple unit tablet or capsule compositions, oil solutions, suspensions, emulsions, microcapsules, microspheres, nanoparticles, patches, and liposomes).

Solid Dosage Forms for Oral Use

Formulations for oral use include tablets containing the composition of the invention in a mixture with non-toxic pharmaceutically acceptable excipients. These excipients may be, for example, inert diluents or fillers (e.g., sucrose, microcrystalline cellulose, starches including potato starch, calcium carbonate, sodium chloride, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., acacia, alginic acid, sodium alginate, gelatin, starch, pregelatinized starch, microcrystalline cellulose, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., stearic acid, silicas, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). A time delay material such as, e.g., glyceryl monostearate or glyceryl distearate may be employed.

The solid tablet compositions may include a coating adapted to protect the composition from unwanted chemical changes, (e.g., chemical degradation prior to the release of the active drug substance). The coating may be applied on the solid dosage form in a similar manner as that described in Encyclopedia of Pharmaceutical Technology.

Drugs may be mixed together in the tablet, or may be partitioned. For example, a first drug is contained on the inside of the tablet, and a second drug is on the outside, such that a substantial portion of the second drug is released prior to the release of the first drug.

Formulations for oral use may also be presented as chewable tablets, or as hard gelatin capsules wherein the active ingredient is mixed with an inert solid diluent (e.g., potato starch, microcrystalline cellulose, calcium carbonate, calcium phosphate or kaolin), or as soft gelatin capsules wherein the active ingredient is mixed with water or an oil medium, for example, liquid paraffin, or olive oil. Powders and granulates may be prepared using the ingredients mentioned above under tablets and capsules in a conventional manner.

Controlled release compositions for oral use may, e.g., be constructed to release the active drug by controlling the dissolution and/or the diffusion of the active drug substance.

Dissolution or diffusion controlled release can be achieved by appropriate coating of a tablet, capsule, pellet, or granulate formulation of drugs, or by incorporating the drug into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing one or more of the drugs of the claimed combinations may also be in the form of a buoyant tablet or capsule (i.e., a tablet or capsule that, upon oral administration, floats on top of the gastric content for a certain period of time). A buoyant tablet formulation of the drug(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Liquids for Oral Administration

Powders, dispersible powders, or granules suitable for preparation of an aqueous suspension by addition of water are convenient dosage forms for oral administration. Formulation as a suspension provides the active ingredient in a mixture with a dispersing or wetting agent, suspending agent, and one or more preservatives. Suitable suspending agents are, for example, sodium carboxymethylcellulose, methylcellulose, sodium alginate, and the like.

Parenteral Compositions

The pharmaceutical composition may also be administered parenterally by injection, infusion or implantation (intravenous, intramuscular, subcutaneous, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation or it may be presented as a dry powder to be reconstituted with water or another suitable vehicle before use. Apart from the active drug(s), the composition may include suitable parenterally acceptable carriers and/or excipients. The active drug(s) may be incorporated into microspheres, microcapsules, nanoparticles, liposomes, or the like for controlled release. The composition may include suspending, solubilizing, stabilizing, pH-adjusting agents, and/or dispersing agents.

The pharmaceutical compositions according to the invention may be in the form suitable for sterile injection. To prepare such a composition, the suitable active drug(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution. The aqueous formulation may also contain one or more preservatives (e.g., methyl, ethyl or n-propyl p-hydroxybenzoate). In cases where one of the drugs is only sparingly or slightly soluble in water, a dissolution enhancing or solubilizing agent can be added, or the solvent may include 10-60% w/w of propylene glycol or the like.

Controlled release parenteral compositions may be in form of aqueous suspensions, microspheres, microcapsules, magnetic microspheres, oil solutions, oil suspensions, or emulsions. Alternatively, the active drug(s) may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutamine). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(glycolic acid) or poly(ortho esters)).

Alternative Routes

Although less preferred and less convenient, other administration routes, and therefore other formulations, may be contemplated. In this regard, for rectal application, suitable dosage forms for a composition include suppositories (emulsion or suspension type), and rectal gelatin capsules (solutions or suspensions). In a typical suppository formulation, the active drug(s) are combined with an appropriate pharmaceutically acceptable suppository base such as cocoa butter, esterified fatty acids, glycerinated gelatin, and various water-soluble or dispersible bases like polyethylene glycols. Various additives, enhancers, or surfactants may be incorporated.

The pharmaceutical compositions may also be administered topically on the skin for percutaneous absorption in dosage forms or formulations containing conventionally non-toxic pharmaceutical acceptable carriers and excipients including microspheres and liposomes. The formulations include creams, ointments, lotions, liniments, gels, hydrogels, solutions, suspensions, sticks, sprays, pastes, plasters, and other kinds of transdermal drug delivery systems. The pharmaceutically acceptable carriers or excipients may include emulsifying agents, antioxidants, buffering agents, preservatives, humectants, penetration enhancers, chelating agents, gel-forming agents, ointment bases, perfumes, and skin protective agents.

The preservatives, humectants, penetration enhancers may be parabens, such as methyl or propyl p-hydroxybenzoate, and benzalkonium chloride, glycerin, propylene glycol, urea, etc.

The pharmaceutical compositions described above for topical administration on the skin may also be used in connection with topical administration onto or close to the part of the body that is to be treated. The compositions may be adapted for direct application or for application by means of special drug delivery devices such as dressings or alternatively plasters, pads, sponges, strips, or other forms of suitable flexible material.

Dosages and Duration of the Treatment

It will be appreciated that the drugs of the combination may be administered concomitantly, either in the same or different pharmaceutical formulation or sequentially. If there is sequential administration, the delay in administering the second (or additional) active ingredient should not be such as to lose the benefit of the efficacious effect of the combination of the active ingredients. A minimum requirement for a combination according to this description is that the combination should be intended for combined use with the benefit of the efficacious effect of the combination of the active ingredients. The intended use of a combination can be inferred by facilities, provisions, adaptations and/or other means to help using the combination according to the invention.

Therapeutically effective amounts of the drugs in a combination of this invention include, e.g., amounts that are effective for reducing Alzheimer's disease symptoms, halting or slowing the progression of the disease once it has become clinically manifest, or prevention or reduction of the risk of developing the disease.

Although the active drugs of the present invention may be administered in divided doses, for example two or three times daily, a single daily dose of each drug in the combination is preferred, with a single daily dose of all drugs in a single pharmaceutical composition (unit dosage form) being most preferred.

Administration can be one to several times daily for several days to several years, and may even be for the life of the patient. Chronic or at least periodically repeated long-term administration is indicated in most cases.

The term "unit dosage form" refers to physically discrete units (such as capsules, tablets, or loaded syringe cylinders) suitable as unitary dosages for human subjects, each unit containing a predetermined quantity of active material or materials calculated to produce the desired therapeutic effect, in association with the required pharmaceutical carrier.

The amount of each drug in a preferred unit dosage composition depends upon several factors including the administration method, the body weight and the age of the patient, the stage of the disease, the risk of potential side effects considering the general health status of the person to be treated. Additionally, pharmacogenomic (the effect of genotype on the pharmacokinetic, pharmacodynamic or efficacy profile of a therapeutic) information about a particular patient may affect the dosage used.

Except when responding to especially impairing cases, where higher dosages may be required, the preferred dosage of each drug in the combination will usually lie within the range of doses not above the dosage usually prescribed for long-term maintenance treatment or proven to be safe in phase 3 clinical studies.

One remarkable advantage of the invention is that each compound may be used at low doses in a combination therapy, while producing, in combination, a substantial clinical benefit to the patient. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably 1/10 of therapeutic doses. In particular examples, doses as low as 1/20, 1/30, 1/50, 1/100, or even lower, of therapeutic doses are used.

At such sub-therapeutic dosages, the compounds would exhibit no side effect, while the combination(s) according to the invention are fully effective in treating Alzheimer's disease.

A preferred dosage corresponds to amounts from 1% up to 50% of those usually prescribed for long-term maintenance treatment.

The most preferred dosage may correspond to amounts from 1% up to 10% of those usually prescribed for long-term maintenance treatment.

Specific examples of dosages of drugs for use in the invention are provided below:

Acamprosate between 1 and 1000 mg/day, preferably less than 400 mg per day, more preferably less than 200 mg/day, even more preferably less than 50 mg/day, such dosages being particularly suitable for oral administration.

Baclofen between 0.01 to 150 mg per day, preferably less than 100 mg per day, more preferably less than 50 mg/day, even more preferably less than 25 mg/day, such dosages being particularly suitable for oral administration.

Aminocaproic Acid orally from about 0.1 g to 2.4 g per day,
Bromocriptine orally from about 0.01 to 10 mg per day,
Diethylcarbamazine orally from about 0.6 to 600 mg per day,
Cabergoline orally from about 1 to 10 µg per day,
Cinacalcet orally from about 0.3 to 36 mg per day,
Cinnarizine orally from about 0.6 to 23 mg per day,
Dyphylline orally from about 9 to 320 mg per day,
Eplerenone orally from about 0.25 to 10 mg per day,
Ifenprodil orally from about 0.4 to 6 mg per day,
Leflunomide orally from about 0.1 to 10 mg per day,
Levosimendan orally from about 0.04 to 0.8 mg per day,
Mexiletine orally from about 6 to 120 mg per day,
Moxifloxacin orally from about 4 to 40 mg per day,
Phenformin orally from about 0.25 to 15 mg per day,
Quinacrine orally from about 1 to 30 mg per day,
Sulfisoxazole orally from about 20 to 800 mg per day,
Sulodexide orally from about 0.05 to 40 mg per day,
Terbinafine orally from about 2.5 to 25 mg per day,
Torasemide orally from about 0.05 to 4 mg per day,
Trimetazidine orally from about 0.4 to 6 mg per day,
Zonisamide orally from about 0.5 to 50 mg per day.

When the composition comprises, as active ingredient, only Baclofen and Acamprosate, these two compounds may be used in different ratios, e.g., at a weight ratio Acamprosate/Baclofen comprised between from 0.05 to 1000 (W:W), preferably between 0.05 to 100 (W:W), more preferably between 0.05 to 50 (W:W).

It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention.

The following examples are given for purposes of illustration and not by way of limitation.

EXAMPLES

The care and husbandry of animals as well as the experimentations are performed according to the guidelines of the Committee for Research and Ethical Issue of the I.A.S.P. (1983).

A) Treatment of Diseases Related to Aβ Toxicity

In this series of experiments, candidate combinations have been tested for their ability to prevent or reduce the toxic effects of human $A\beta_{1-42}$. $A\beta_{1-42}$ is the full length peptide that constitutes aggregates found in biopsies from human patients afflicted with AD. The effect is determined on various cell types, to further document the activity of the combinations in in vitro models which illustrate different physiological features of AD. In vivo studies are also performed in a mouse model for AD confirming this protective effect by evaluating the effect of the combinations on i) the cognitive performance of animals and ii) on molecular hallmarks (apoptosis induction, oxidative stress induction, inflammation pathway induction) of AD.

I. Baclofen-Acamprosate Combination Therapies Prevent Toxicity of Human $A\beta_{1-42}$ In Vitro

I.1 Effect on the Toxicity of Human $A\beta_{1-42}$ Peptide on Human HBME Cells.

Human brain microvascular endothelial cell cultures were used to study the protection afforded by candidate compound(s) on $A\beta_{1-42}$ toxicity.

Human brain microvascular endothelial cerebral cells (HBMEC, ScienCell Ref: 1000, frozen at passage 10) were rapidly thawed in a waterbath at +37° C. The supernatant was immediately put in 9 ml Dulbecco's modified Eagle's medium (DMEM; Pan Biotech ref: P04-03600) containing 10% of foetal calf serum (FCS; GIBCO ref 10270-106). Cell suspension was centrifuged at 180×g for 10 min at +4° C. and the pellets were suspended in CSC serum-free medium (CSC serum free, Cell System, Ref: SF-4Z0-500-R, Batch 51407-4) with 1.6% of Serum free RocketFuel (Cell System, Ref: SF-4Z0-500-R, Batch 54102), 2% of Penicillin 10.000 U/ml and Streptomycin 10 mg/ml (PS; Pan Biotech ref: P06-07100 batch 133080808) and were seeded at the density of 20 000 cells per well in 96 well-plates (matrigel layer biocoat angiogenesis system, BD, Ref 354150, Batch A8662) in a final volume of 100 µl. On matrigel support, endothelial cerebral cells spontaneously started the process of capillary network morphogenesis (33).

Three separate cultures were performed per condition, 6 wells per condition.

Test Compounds and Human Amyloid-$\beta_{1-42}$ Treatment

Briefly, $A\beta_{1-42}$ peptide (Bachem, ref: H1368 batch 1010533) was reconstituted in define culture medium at 20 µM (mother solution) and was slowly shacked at +37° C. for 3 days in dark. The control medium was prepared in the same conditions.

After 3 days, human amyloid peptide was used on HBMEC at 2.5 µM diluted in control medium (optimal incubation time). The $A\beta_{1-42}$ peptide was added 2 hours after HBMEC seeding on matrigel for 18 hours incubation.

One hour after HBMEC seeding on matrigel, test compounds and VEGF-165 were solved in culture medium (+0.1% DMSO) and then pre-incubated with HBMEC for 1 hour before the $A\beta_{1-42}$ application (in a final volume per culture well of 100 µl). One hour after test compounds or VEGF incubation (two hours after cell seeding on matrigel), 100 µl of $A\beta_{1-42}$ peptide was added to a final concentration of 2.5 µM diluted in control medium in presence of test compounds or VEGF (in a 200 µl total volume/well), in order to avoid further drug dilutions.

Organization of Cultures Plates

VEGF-165 known to be a pro-angiogenic isoform of VEGF-A, was used for all experiment in this study as reference compound. VEGF-165 is one of the most abundant VEGF isoforms involved in angiogenesis. VEGF was used as reference test compound at 10 nM (FIG. 1).

The following conditions were assessed:
Negative Control: medium alone+0.1% DMSO
Intoxication: amyloid-$\beta_{1-42}$ (2.5 µM) for 18 h
Positive control: VEGF-165 (10 nM) (1 reference compound/culture) 1 hr before the $A\beta_{1-42}$ (2.5 µM) addition for a 18 h incubation time.
Test compounds: Test compound(s) 1 hr before the $A\beta_{1-42}$ (2.5 µM) addition for a 18 h incubation time.

Capillary Network Quantification

Per well, 2 pictures with 4× lens were taken using InCell Analyzer™ 1000 (GE Healthcare) in light transmission. All images were taken in the same conditions. Analysis of the angiogenesis networks was done using Developer software (GE Healthcare). The total length of capillary network was assessed.

Data Processing

Data were expressed in percentage of control conditions (no intoxication, no amyloid=100%) in order to express the amyloid injury. All values were expressed as mean+/−SEM (s.e.mean) of the 3 cultures (n=6 wells per condition). Statistic analyses were done on the different conditions (ONE-WAY ANOVA followed by the Dunnett's test when it was allowed, Statview software version 5.0).

Results

Baclofen-Acamprosate combination gives a significant protective effect against toxicity of human $A\beta_{1-42}$ peptide in HBMEC model (a reduction of 24% of $A\beta_{1-42}$ peptide injury is observed), as shown in FIG. 2. The results clearly show that the intoxication by human amyloid peptide ($A\beta_{1-42}$ 2.5 µM) is significantly prevented by the drug combination whereas, at those concentrations, the drugs alone have no significant effect on intoxication in the experimental conditions described above.

Figure 3:
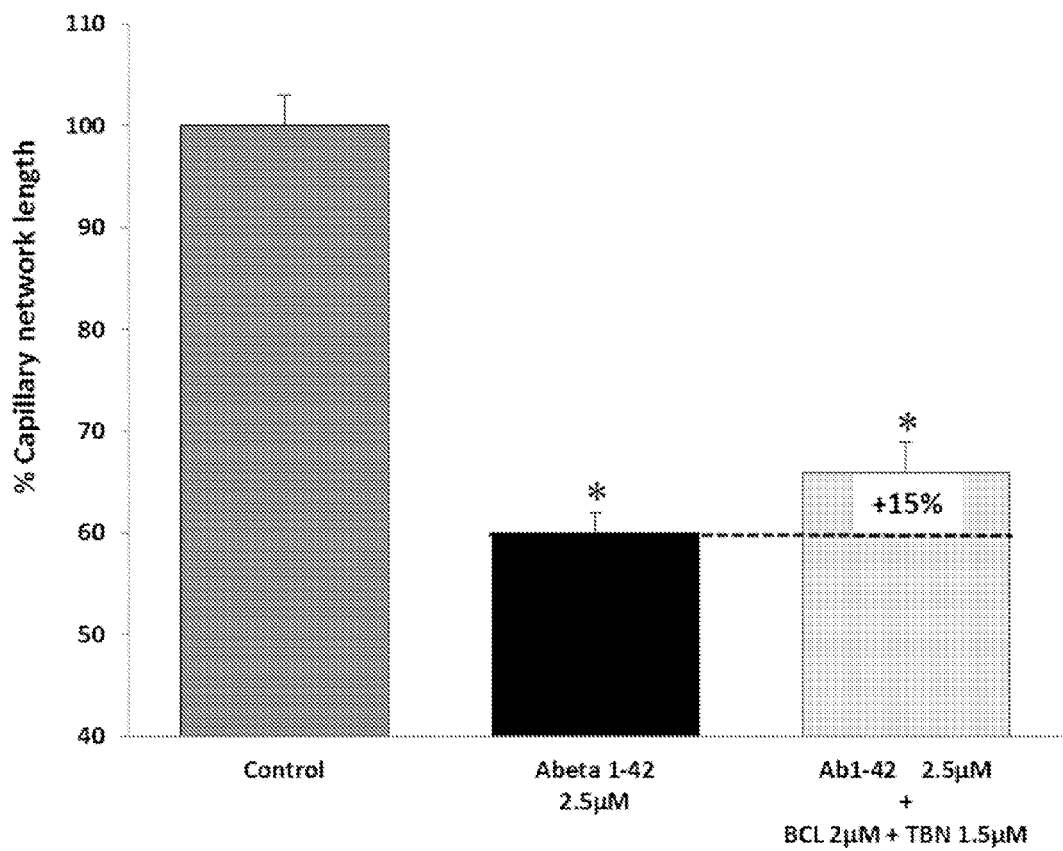
FIG. 3: Effect of Baclofen (BCL) and Terbinafine (TBN) combination therapy on the total length of capillary network in beta-amyloid intoxicated HBMEC cultures. The human amyloid peptide ($A\beta_{1-42}$ 2.5 µM) produces a significant intoxication, above 40%, compared to vehicle-treated cells. This intoxication is prevented by the combination of Terbinafine and Baclofen. *: $p<0.05$: significantly different from control (no intoxication).

Conversely, combination of Baclofen and Terbinafine (which is presented here only for the sake of comparison) affords a weaker protection (a reduction of 15% of $A\beta_{1-42}$ peptide injury is observed) against $A\beta_{1-42}$ (FIG. 3).

Thus, although these two combinations allow a protection against $A\beta_{1-42}$, the combination Baclofen-Acamprosate stands out clearly. Indeed, these drugs at concentrations having no effect alone allow significant protection of human HBME cells against $A\beta_{1-42}$ when used in combination. Furthermore, the Baclofen-Acamprosate combination is more effective than the Baclofen-Terbinafine combination. Such an effect of Baclofen and Acamprosate represents a remarkable improvement by 60% in comparison to e.g., the effect of the combination of Baclofen-Terbinafine.

Moreover, concentration of Baclofen used in the Baclofen-Acamprosate combination is much lower than the concentration of Baclofen used in the Baclofen-Terbinafine combination (25-fold reduction).

I.2 Effect on the Toxicity of Human $A\beta_{1-42}$ Peptide on Primary Cortical Neuron Cells.

Culture of Primary Cortical Neurons

Rat cortical neurons were cultured as described by Singer et al. (47). Briefly pregnant female rats of 15 days gestation were killed by cervical dislocation (Rats Wistar) and the foetuses were removed from the uterus. The cortex was removed and placed in ice-cold medium of Leibovitz (L15) containing 2% of Penicillin 10.000 U/ml and Streptomycin 10 mg/ml and 1% of bovine serum albumin (BSA). Cortexes were dissociated by trypsin for 20 min at 37° C. (0.05%). The reaction was stopped by the addition of Dulbecco's modified Eagle's medium (DMEM) containing DNase1 grade II and 10% of foetal calf serum (FCS). Cells were then mechanically dissociated by 3 serial passages through a 10 ml pipette and centrifuged at 515×g for 10 min at +4° C. The supernatant was discarded and the pellet of cells was re-suspended in a defined culture medium consisting of Neurobasal supplemented with B27 (2%), L-glutamine (0.2 mM), 2% of PS solution and 10 ng/ml of BDNF. Viable cells were counted in a Neubauer cytometer using the trypan blue exclusion test. The cells were seeded at a density of 30 000 cells/well in 96 well-plates (wells were pre-coated with poly-L-lysine (10 µg/ml)) and were cultured at +37° C. in a humidified air (95%)/CO2 (5%) atmosphere.

Three independent cultures will be performed per condition, 6 wells per condition.

Test Compounds and Human Amyloid-α1-42 Treatment

Briefly, Aβ$_{1-42}$ peptide was reconstituted in define culture medium at 40 μM (mother solution) and was slowly shaken at +37° C. for 3 days in dark. The control medium was prepared in the same conditions.

After 3 days, the solution was used on primary cortical neurons as follows:

After 10 days of neuron culture, test compounds were solved in culture medium (+0.1% DMSO) and then pre-incubated with neurons for 1 hour before the Aβ$_{1-42}$ application (in a final volume per culture well of 100 μl). One hour after test compound(s) incubation, 100 μl of Aβ$_{1-42}$ peptide was added to a final concentration of 10 μM diluted in presence of drug(s), in order to avoid further test compound(s) dilutions. Cortical neurons were intoxicated for 24 hours. Three separate cultures were performed per condition, 6 wells per condition.

BDNF (50 ng/ml) and Estradiol-β (150 nM) were used as positive control and reference compounds respectively. Three separate cultures will be performed per condition, 12 wells per condition.

Organization of Cultures Plates

Figure 4:
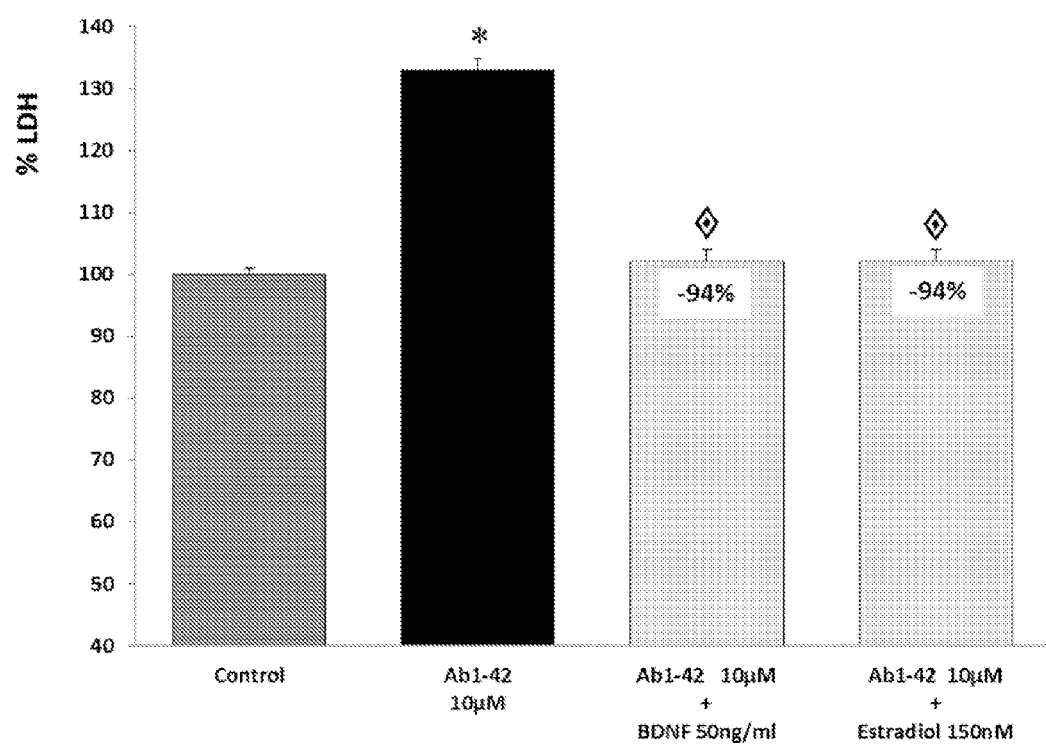
FIG. 4: Validation of the experimental model of human βamyloid's toxicity on neuronal cells used for drug screening. One hour of Estradiol (150 nM) or BDNF (50 ng/mL) pre-treatment significantly protected the neurons from this amyloid injury (~94%), which is considered as a positive control for neuroprotection.*: p<0.05: significantly different from control (no intoxication); ◊: p<0.05, significantly different from $A\beta_{1-42}$ intoxication.

Estradiol-β at 150 nM was used as a positive control (FIG. 4).

Estradiol-β was solved in culture medium and pre-incubated for 1 h before the amyloid-β$_{1-42}$ application.

The following conditions were assessed:
CONTROL PLAQUE: 12 wells/condition
  Negative Control: medium alone+0.1% DMSO
  Intoxication: amyloid-β$_{1-42}$ (10 μM) for 24 h
  Reference compound: Estradiol (150 nM) 1 hr.
DRUG PLATE: 6 wells/condition
  Negative Control: medium alone+0.1% DMSO
  Intoxication: amyloid-β$_{1-42}$ (10 μM) for 24 h
  Test compound(s): test compound(s)—1 hr followed by amyloid-β$_{1-42}$ (10 μM) for 24 h Lactate Dehydrogenase (LDH) Activity Assay 24 hours after intoxication, the supernatant was taken off and analyzed with Cytotoxicity Detection Kit (LDH, Roche Applied Science, ref: 11644793001, batch: 11800300). This colorimetric assay for the quantification of cell toxicity is based on the measurement of lactate dehydrogenase (LDH) activity released from the cytosol of dying cells into the supernatant.

Data Processing

Data were expressed in percentage of control conditions (no intoxication, no amyloid=100%) in order to express the amyloid injury. All values were expressed as mean+/−SEM (s.e.mean) of the 3 cultures (n=6 wells per condition). Statistic analyses were done on the different conditions (ONE-WAY ANOVA followed by the Dunnett's test when it was allowed, Statview software version 5.0).

Results

The combination of Baclofen and Acamprosate induces a significant protective effect against the toxicity of human Aβ$_{1-42}$ peptide (improvement of 34% of cell survival) in primary cortical neuron cells as shown in FIG. 5. The results clearly show that the intoxication by human amyloid peptide (Aβ$_{1-42}$ 10 μM) is significantly prevented by the combination, whereas at those concentrations, Baclofen or Acamprosate, alone, have no significant effect on intoxication.

Figure 6:
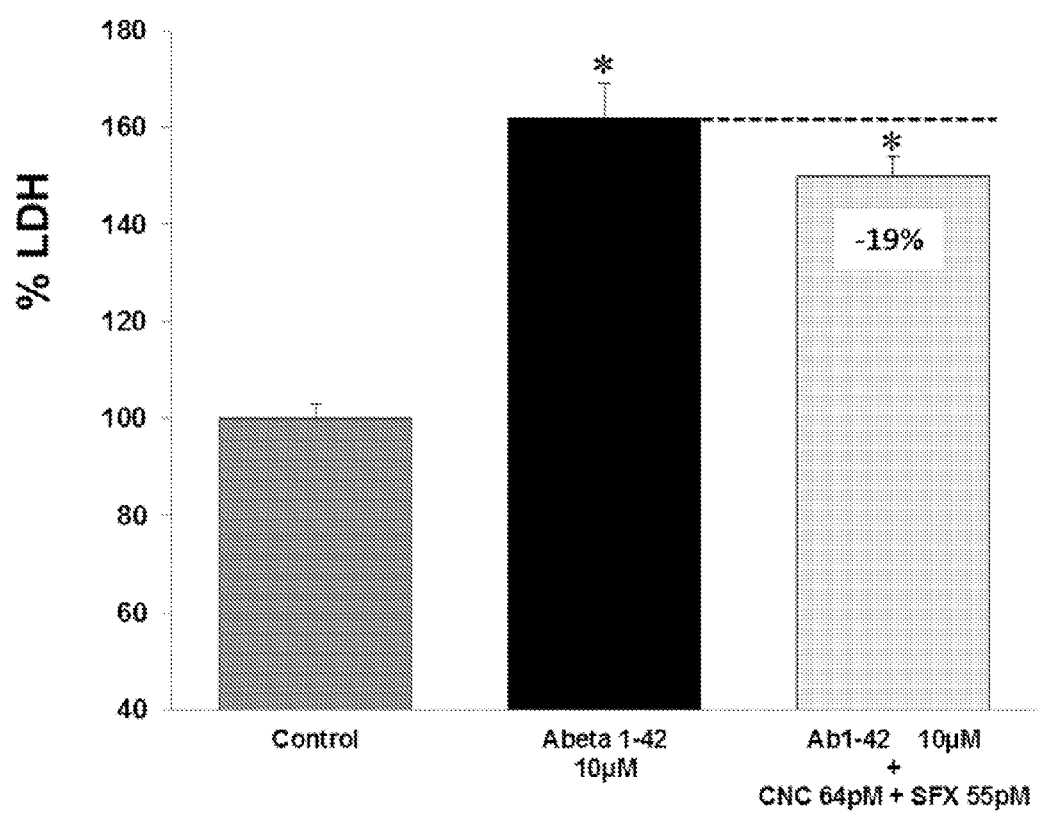
FIG. 6: Effect of Cinacalcet (CNC) and Sulfisoxazole (SFX) combination therapy on LDH release in human $A\beta_{1-42}$ toxicity on rat primary cortical cells. The human amyloid peptide ($A\beta_{1-42}$ 10 μM) produces a significant intoxication compared to vehicle-treated neurons. This intoxication is prevented by the combination of Cinacalcet and Sulfisoxazole. *: p<0.05, significantly different from vehicle.

Conversely, although active in this model, the combination of Sulfisoxazole and Cinacalcet affords a weaker protection against Aβ$_{1-42}$ (19%, FIG. 6).

Thus, while those two combinations allow a protection against Aβ$_{1-42}$, the combination Baclofen-Acamprosate stands out clearly. Indeed, at concentrations having no effect alone, the drugs cause a significant protection of primary cortical neuron cells against Aβ$_{1-42}$ when used in combination. Furthermore, the Baclofen-Acamprosate combination is much more effective than the Sulfisoxazole-Cinacalcet combination. Such an effect of Baclofen and Acamprosate represents a remarkable improvement by 60% in comparison to e.g., the effect of the combination of Sulfisoxazole and Cinacalcet.

Taken together these results show an unexpected and remarkable positive effect of Baclofen-Acamprosate combinations in several in vitro models of Alzheimer's disease. The effect observed is highly superior to that provoked by other Baclofen-based combination therapies (e.g., Baclofen-Terbinafine), or other active combination therapies (Sulfisoxazole-Cinacalcet).

Figure 17:
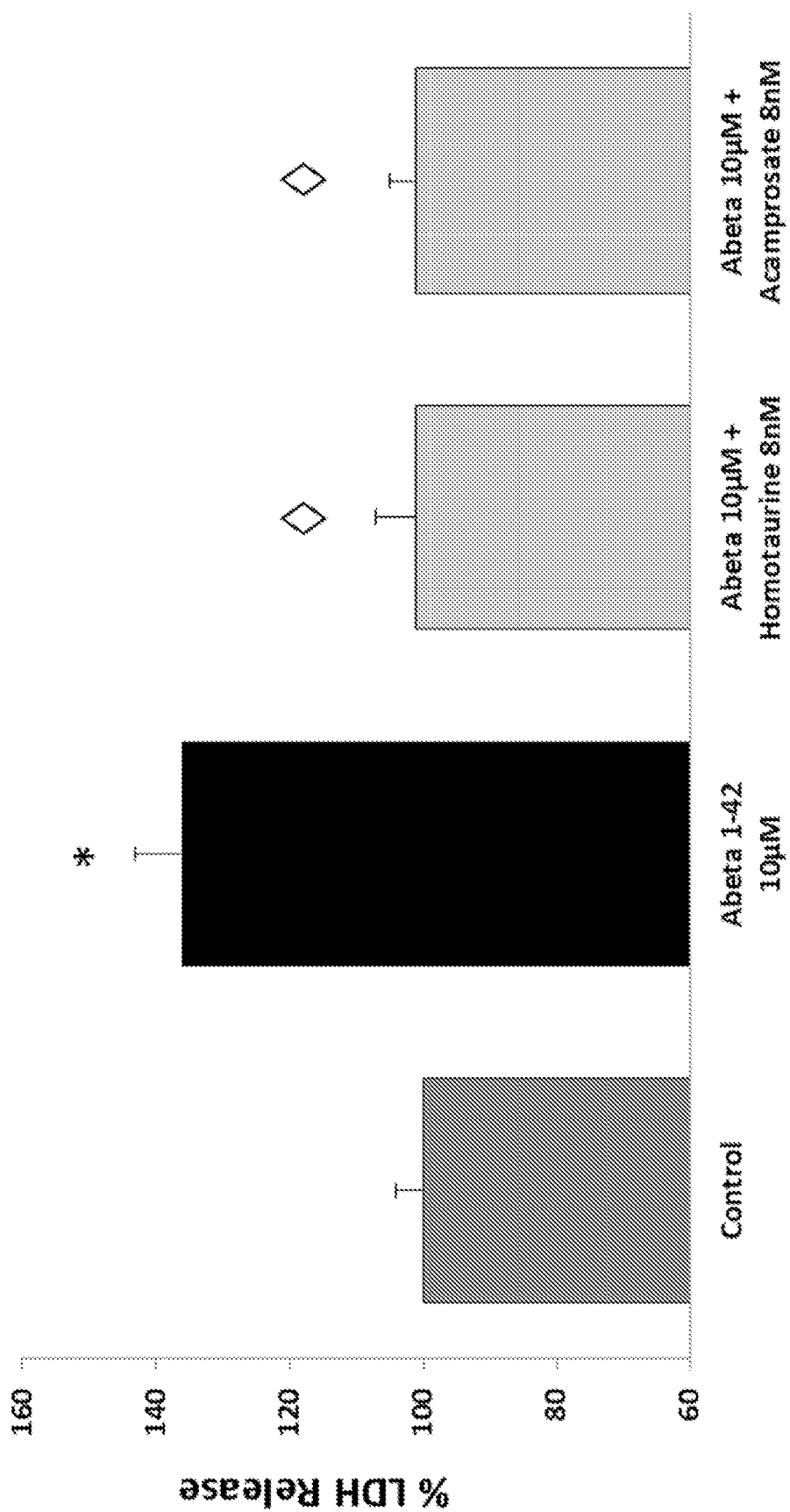
FIG. 17: Comparison of protective effect of Acamprosate and its derivative Homotaurine pre-treatment in human $A\beta_{1-42}$ toxicity assays on rat primary cortical cells. $A\beta_{1-42}$ produces a significant intoxication compared to vehicle-treated neurons. The intoxication is equally significantly prevented by Homotaurine and Acamprosate (99%, 8 nM). ◊: p<0.0001: significantly different from $A\beta_{1-42}$ intoxication.

A comparison of Acamprosate and Homotaurine protection activity on cortical cells has been done (FIG. 17). Those results shown that the derivative of acamprosate, called Homotaurine, allow an effective protection against Aβ$_{1-42}$. In the context of this invention, Baclofen or Acamprosate can thus be substituted by their derivatives, provided that those derivatives are efficient in assay described herein.

I.3. Protection Against the Toxicity of Aβ$_{1-42}$ in a Neurite Growth and Synapse Functionality Model.

Rat cortical neurons were cultured as described by Singer et al. (35). Briefly pregnant female rats of 15 days gestation were killed by cervical dislocation (Rats Wistar) and the foetuses were removed from the uterus. The cortex was removed and placed in ice-cold medium of Leibovitz (L15) containing 2% of Penicillin 10.000 U/ml and Streptomycin 10 mg/ml and 1% of bovine serum albumin (BSA). Cortices were dissociated by trypsin for 20 min at 37° C. (0.05%). The reaction was stopped by the addition of Dulbecco's modified Eagle's medium (DMEM) containing DNase1 grade II and 10% of foetal calf serum (FCS). Cells were then mechanically dissociated by 3 serial passages through a 10 ml pipette and centrifuged at 515×g for 10 min at +4° C. The supernatant was discarded and the pellet of cells was re-suspended in a defined culture medium consisting of Neurobasal supplemented with B27 (2%), L-glutamine (0.2 mM), 2% of PS solution and 10 ng/ml of BDNF. Viable cells were counted in a Neubauer cytometer using the trypan blue exclusion test. The cells were seeded at a density of 30 000 cells/well in 96 well-plates (wells were pre-coated with poly-L-lysine (10 μg/ml)) and were cultured at +37° C. in a humidified air (95%)/CO2 (5%) atmosphere.

After 10 days of culture, cells are incubated with drugs. After 1 hour, cells are intoxicated by 2.504 of beta-amyloid (1-42; Bachem) in defined medium without BDNF but together with drugs. Cortical neurons are intoxicated for 24 hours. BDNF (10 ng/ml) is used as a positive (neuroprotective) control. Three independent cultures were performed per condition, 6 wells per condition.

Neurites Length and Synapse Quantitation

After 24 hours of intoxication, the supernatant is taken off and the cortical neurons are fixed by a cold solution of ethanol (95%) and acetic acid (5%) for 5 min. After permeabilization with 0.1% of saponin, cells are blocked for 2 h with PBS containing 1% foetal calf serum. Then, cells are incubated with monoclonal antibody anti microtubule-associated-protein 2 (MAP-2; Sigma) or with anti synaptophysin (SYN, S5798, Sigma) together with anti PSD95 (P246, Sigma) antibodies in order to quantify synapses. These antibodies stain specifically cell bodies and neurites of neurons of neurons (MAP2) or pre and post synaptic elements (SYN and PSD95, respectively).

These antibodies are revealed with Alexa Fluor 488 goat anti-mouse IgG (Molecular probe). Nuclei of neurons were labeled by a fluorescent marker (Hoechst solution, SIGMA). Per well, 10 pictures are taken using InCell Analyzer™ 1000 (GE Healthcare) with 20× magnification. All pictures are taken in the same conditions. Analysis of the neurite network is done using Developer software (GE Healthcare) in order to assess the total length of neurite network.

Results

Figure 7:
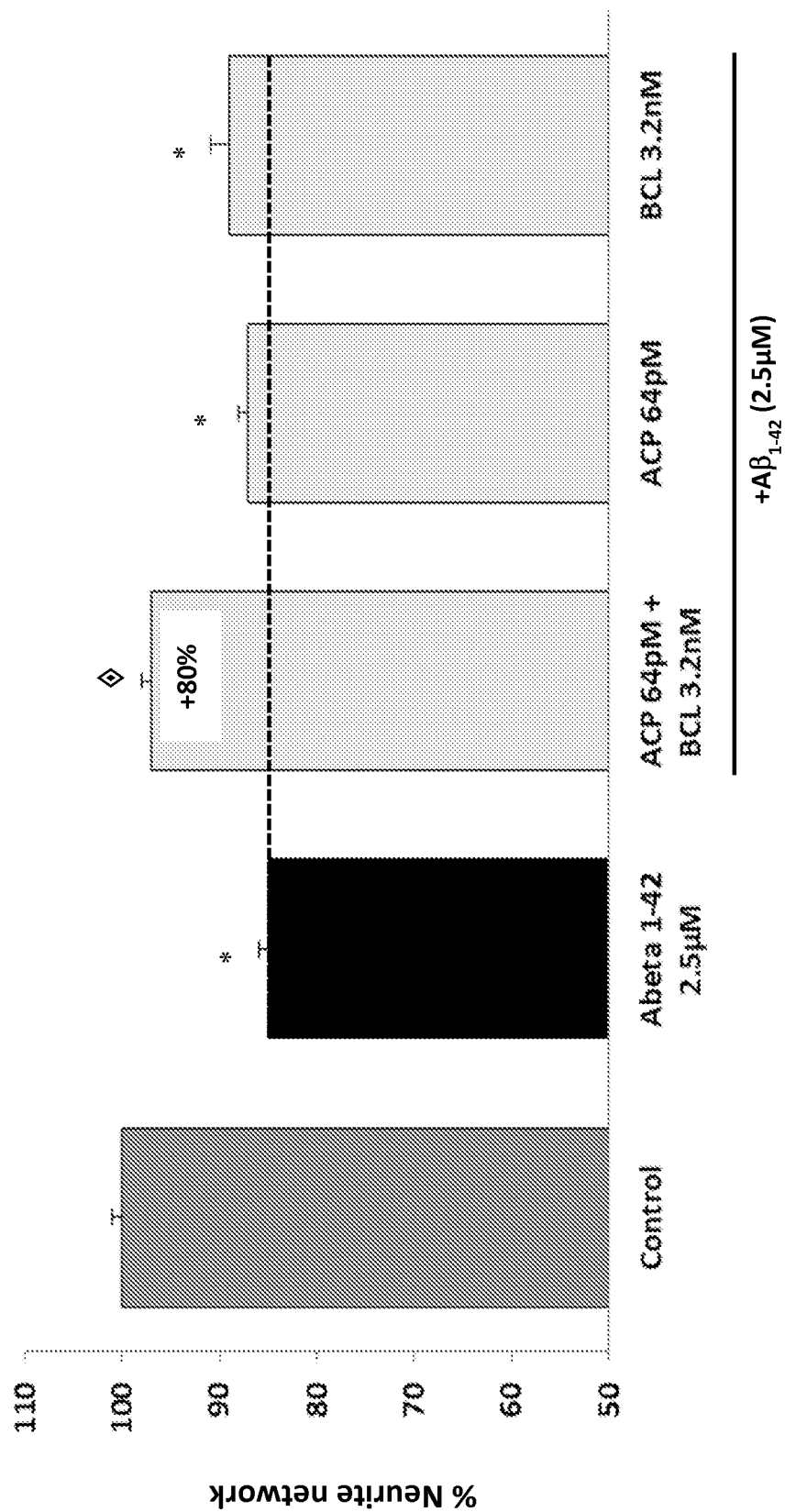
FIG. 7: Effect of Acamprosate (ACP) and Baclofen (BCL) combination therapy on the total length of neurites network in beta-amyloid intoxicated cortical neurons. The human amyloid peptide ($A\beta_{1-42}$ 2.5 μM) produces a significant intoxication, above 15%, compared to vehicle-treated cells. This intoxication is significantly prevented by the combination of Acamprosate and Baclofen whereas, at those concentrations, Acamprosate and Baclofen alone have no significant effect on intoxication. ◊: p<0.05, significantly different from $A\beta_{1-42}$ intoxication; *: p<0.05, significantly different from vehicle (ANOVA+Dunnett Post-Hoc test).

The combination of Baclofen and Acamprosate induces a significant protective effect against the toxicity of human $A\beta_{1-42}$ peptide (improvement of 80% of neurites network) in primary cortical neuron cells as shown in FIG. 7. The results clearly show that the intoxication by human amyloid peptide ($A\beta_{1-42}$ 2.5 μM) is significantly prevented by the combination, whereas at those concentrations, Baclofen or Acamprosate, alone, have no significant effect on intoxication.

Furthermore, the total length of neurite network treated with this combination is no more significantly different from control cells. Hence, this combination allows an effective protection of cortical neuron cells against the toxicity of human $A\beta_{1-42}$ peptide but also a neurite growth comparable to a sane cortical neuron cell.

II. Baclofen-Acamprosate Combination Therapies Prevent Toxicity of Human $A\beta_{25-35}$ In Vivo Animals Male Swiss mice are used throughout the study. Animals are housed in plastic cages, with free access to laboratory chow and water, except during behavioural experiments, and kept in a regulated environment, under a 12 h light/dark cycle (light on at 8:00 a.m.). Experiments are carried out in a soundproof and air-regulated experimental room, to which mice have been habituated at least 30 min before each experiment.

Combinatory Treatment

Drug(s) is/are daily administered by gavage (per os). The β 25-35 peptide and scrambled β 25-35 peptide (control) have been dissolved in sterile bidistilled water, and stored at −20° C. until use. The β-amyloid peptides are then administered intracerebroventricularly (i.c.v.). In brief, each mouse is anaesthetized lightly with ether, and a gauge stainless-steel needle is inserted unilaterally 1 mm to the right of the midline point equidistant from each eye, at an equal distance between the eyes and the ears and perpendicular to the plane of the skull. Peptides or vehicle are delivered gradually within approximately 3 s. Mice exhibit normal behaviour within 1 min after injection. The administration site is checked by injecting Indian ink in preliminary experiments. Neither insertion of the needle, nor injection of the vehicle have a significant influence on survival, behavioral responses or cognitive functions.

Drug(s) Treatment

On day −1, i.e. 24 h before the $A\beta_{25-35}$ peptide injection, drug combinations or the vehicle solution are administered per os by gavage twice daily (at 8:00 am and 6:00 pm).

On day 0 (at 10:00 am), mice are injected i.c.v. with Aβ25-35 peptide or scrambled Aβ25-35 peptide (control) in a final volume of 3 μl (3 mM).

Between day 0 and day 7, drugs, drugs combination or the vehicle solution are administered per os by gavage once or twice daily (at 8:00 am and 6:00 pm). One animal group receives donepezil (reference compound—1 mg/kg/day) per os by gavage in a single injection (at 8:00 am). Drugs are solubilized in water and freshly prepared just before each gavage administration.

On day 7, all animals are tested for the spontaneous alternation performance in the Y-maze test, an index of spatial working memory.

On day 7 and 8, the contextual long-term memory of the animals is assessed using the step-down type passive avoidance procedure.

On day 8, animals are sacrificed. Their brain is dissected and kept at −80° C. for further analysis.

Combinations Enhance Behavioral and Cognitive Performances of Intoxicated Animals Spontaneous Alternation Performances-Y Maze Test On day 7, all animals are tested for spontaneous alternation performance in the Y-maze, an index of spatial working memory. The Y-maze is made of grey polyvinylchloride. Each arm is 40 cm long, 13 cm high, 3 cm wide at the bottom, 10 cm wide at the top, and converging at an equal angle. Each mouse is placed at the end of one arm and allowed to move freely through the maze during an 8 min session. The series of arm entries, including possible returns into the same arm, are checked visually. An alternation is defined as entries into all three arms on consecutive occasions. The number of maximum alternations is therefore the total number of arm entries minus two and the percentage of alternation is calculated as (actual alternations/maximum alternations)×100. Parameters include the percentage of alternation (memory index) and total number of arm entries (exploration index). Animals that show an extreme behavior (Alternation percentage <25% or >85% or number of arm entries <10) are discarded. Usually, it accounts for 0-5% of the animals. This test incidentally serves to analyze at the behavioral level the impact and the amnesic effect induced in mice by the Aβ25-35 injection.

Passive Avoidance Test

The apparatus is a two-compartment (15×20×15 cm high) box with one illuminated with white polyvinylchloride walls and the other darkened with black polyvinylchloride walls and a grid floor. A guillotine door separates each compartment. A 60 W lamp positioned 40 cm above the apparatus lights up the white compartment during the experiment. Scrambled footshocks (0.3 mA for 3 s) could be delivered to the grid floor using a shock generator scrambler (Lafayette Instruments, Lafayette, USA). The guillotine door is initially closed during the training session. Each mouse is placed into the white compartment. After 5 s, the door raises. When the mouse enters the darkened compartment and places all its paws on the grid floor, the door closes and the footshock is delivered for 3 s. The step-through latency, that is, the latency spent to enter the darkened compartment, and the number of vocalizations is recorded. The retention test is carried out 24 h after training. Each mouse is placed again into the white compartment. After 5 s the doors is raised, the step-through latency and the escape latency, i.e. the time spent to return into the white compartment, are recorded up to 300 s.

Positive results are observed in behavioural performances and biochemical assays performed 7 days after β25-35 peptide icy injection.

Figure 8:
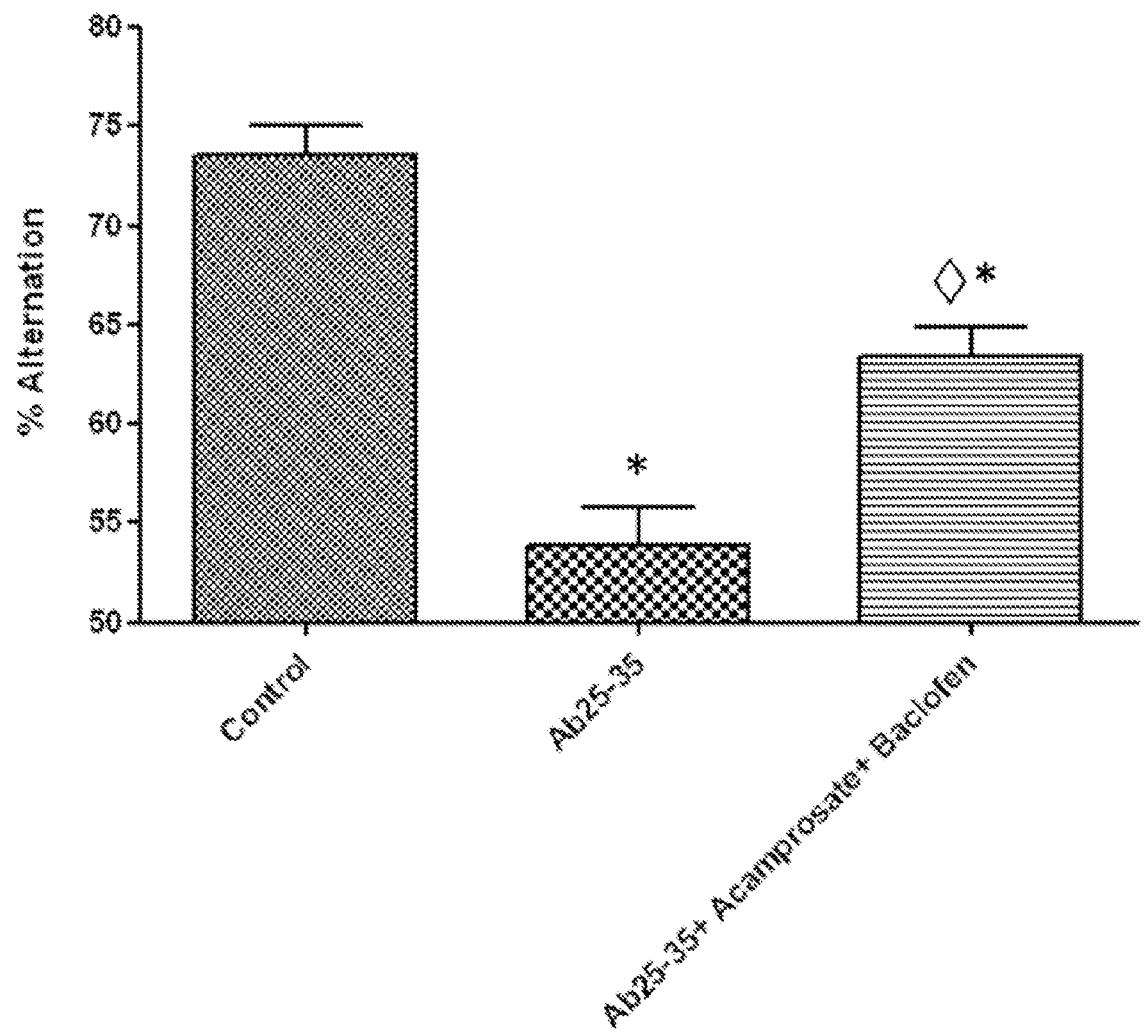
FIG. 8: Effect of Acamprosate and Baclofen combination therapy on behaviour as defined by Y-maze test. The amyloid peptide produces a significant decrease in cognition as measured by percentage of alternation (53.8% versus 73.5%). This deleterious effect is significantly prevented (48.2% of protection) by the combination of Acamprosate (0.2 mg/kg/day) and Baclofen (3 mg/kg/day). ◊: p<0.05, significantly different from $A\beta_{25-35}$ intoxication; *: p<0.05, significantly different from vehicle (ANOVA+Dunnett Post-Hoc test).
Figure 9:
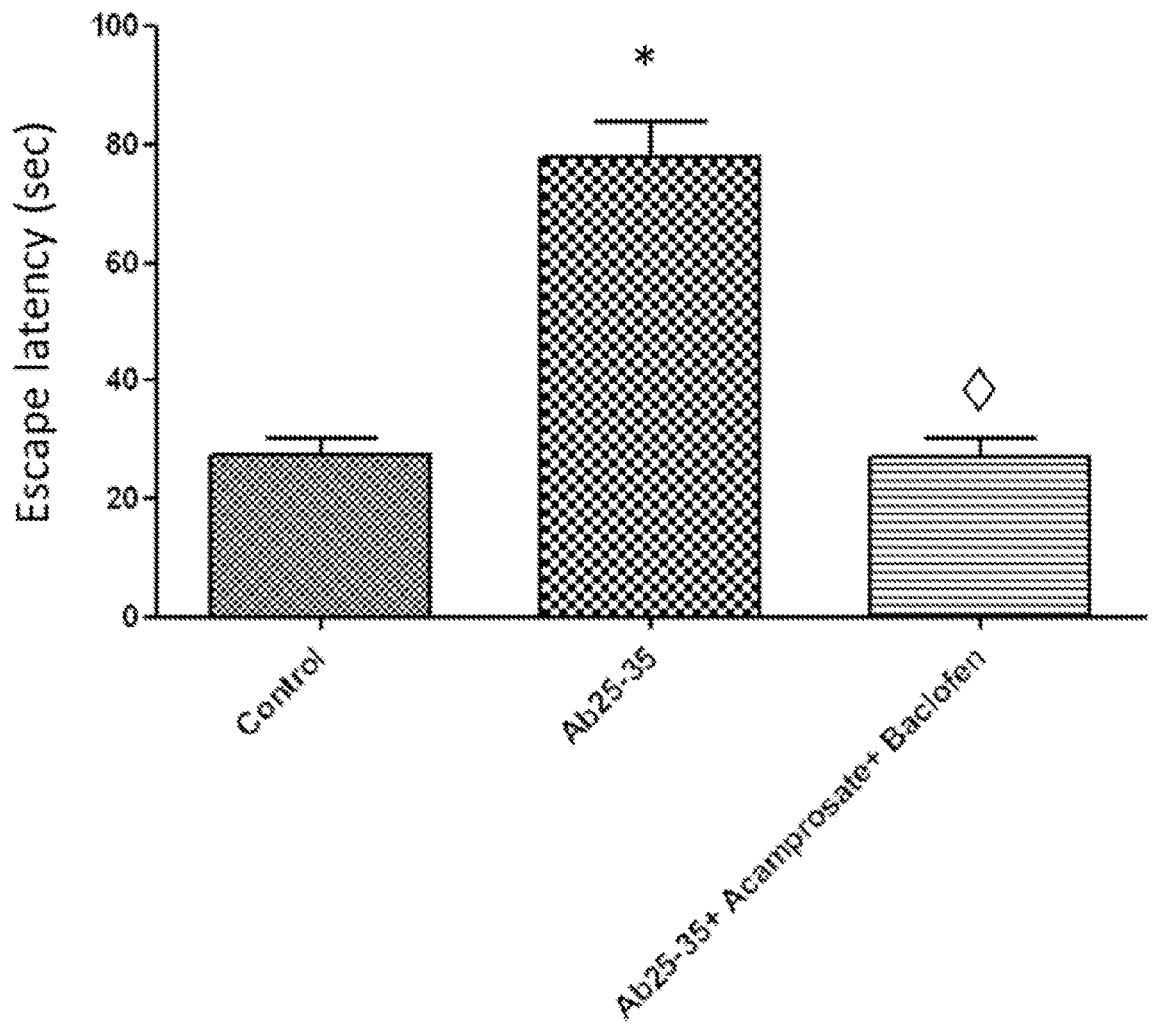
FIG. 9: Effect of Acamprosate and Baclofen combination therapy on memory as defined by passive avoidance (escape latency). The amyloid peptide produces a significant decrease in memory performances as measured by escape latency compared to control. This deleterious effect is significantly prevented (complete protection) by the combination of Acamprosate (0.2 mg/kg) and Baclofen (3 mg/kg). ◊: p<0.05, significantly different from $A\beta_{25-35}$ intoxication; *: p<0.05, significantly different from vehicle (ANOVA+Dunn's test).
Figure 10:
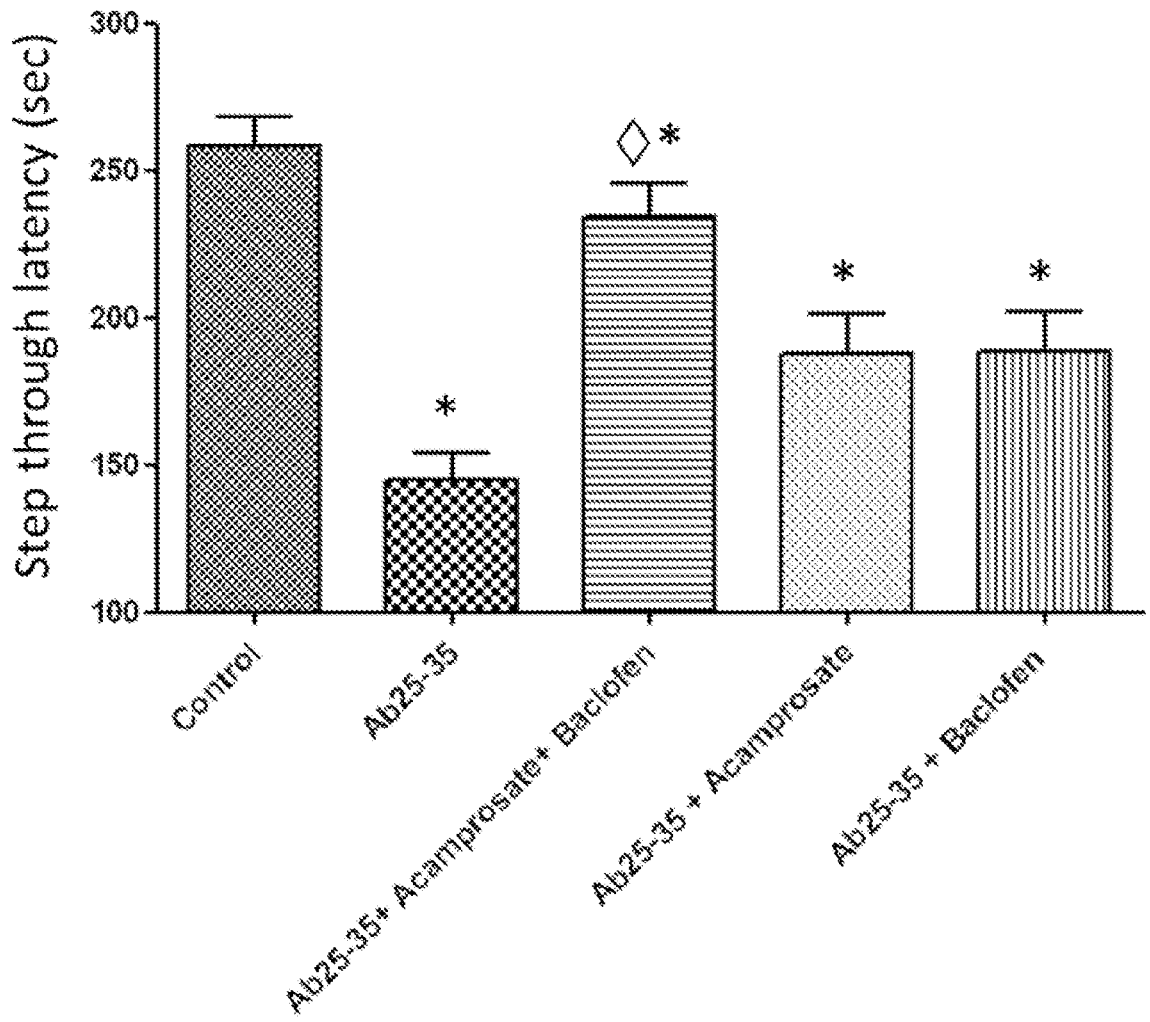
FIG. 10: Effect of Acamprosate and Baclofen combination therapy on memory as defined by passive avoidance (step-through latency). The amyloid peptide produces a significant decrease in memory performances as measured by step-through latency, above 44%, compared to control. This deleterious effect is significantly prevented (78.8% of protection effect) by the combination of Acamprosate (0.2 mg/kg) and Baclofen (3 mg/kg) whereas, at those concentrations, Acamprosate and Baclofen alone have a lower effect on intoxication. ◊: p<0.05, significantly different from $A\beta_{25-35}$ intoxication; *: p<0.05, significantly different from vehicle (ANOVA+Dunn's test).
Figure 11:
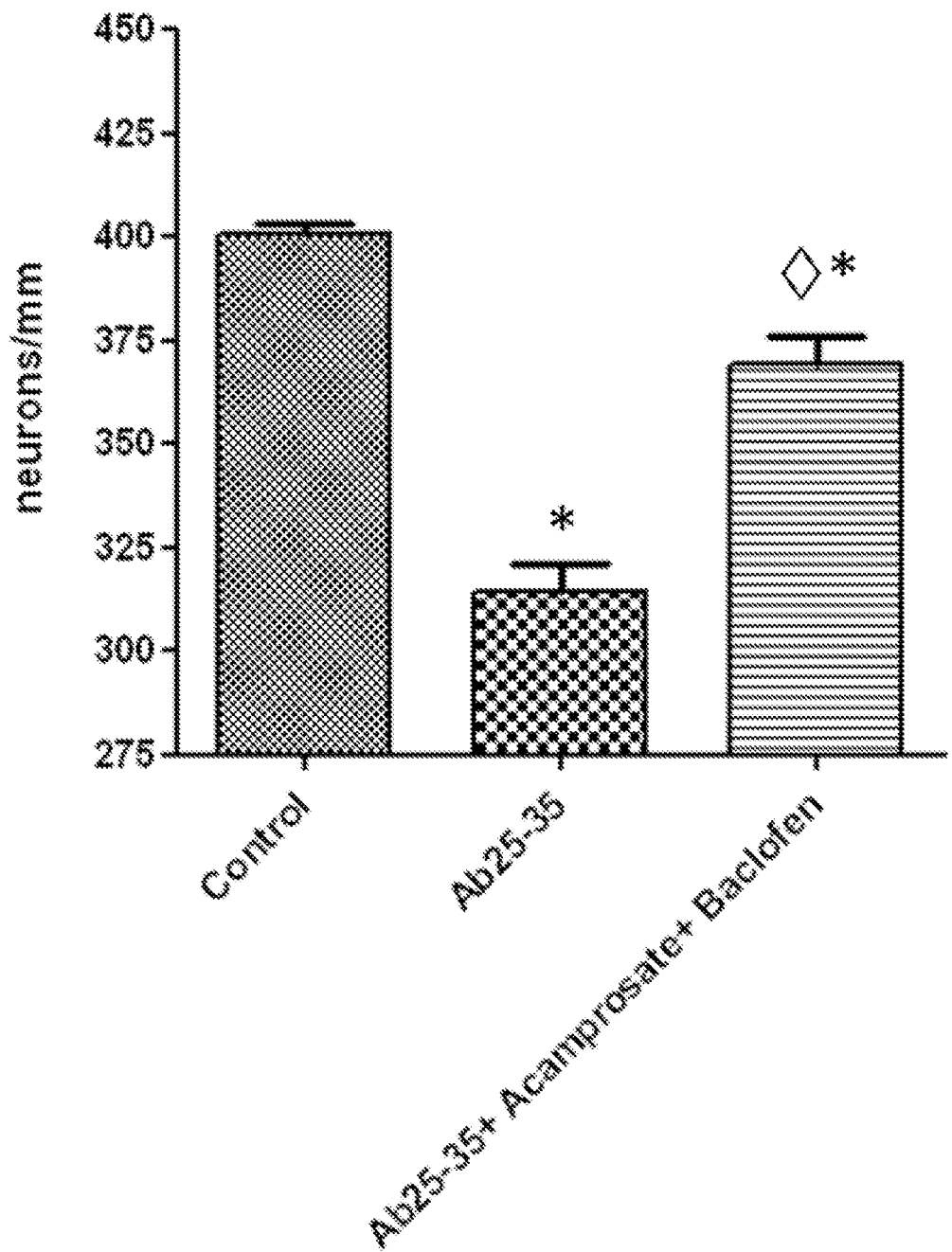
FIG. 11: Effect of Acamprosate and Baclofen combination therapy on neuron's density in hippocampus. The amyloid peptide produces a significant decrease neuronal density as measured by the number of neurons per millimeter in hippocampus, above 21%, compared to control. This neuronal injury is significantly prevented (63.2% of injured neurons are protected) by the combination of Acamprosate (0.2 mg/kg) and Baclofen (3 mg/kg). ◊: p<0.05, significantly different from $A\beta_{25-35}$ intoxication; *: p<0.05, significantly different from vehicle (ANOVA+Dunnett Post-Hoc test).

The combination of Baclofen and Acamprosate induces a significant protective effect on behavioral and cognitive performances of intoxicated animals as shown in FIGS. 8, 9 & 10.

In FIG. 8, with only 53.8% of alternation, intoxicated mice exhibit a strongly impaired spatial working memory compared to control. With an improvement of more than 48% of their percentage of alternation compared to control, the impairment is significantly prevented on mice treated with Baclofen and Acamprosate.

Similarly, FIGS. 9 & 10 show that intoxicated animals exhibit impaired behavioral and cognitive performances according to their score in escape latency and step-through latency respectively. In both tests, the combination of Baclofen and Acamprosate allows a significant correction of the impairment. The escape latency of mice treated with this combination is no more significantly different from control mice (FIG. 9) and step through latency (FIG. 10) is significantly increased by combinations of the invention with an enhanced effect of the combination compared to drugs alone.

Memory impairment is the early feature of Alzheimer disease and these results clearly show that the toxic effect of amyloid peptide on behavioral and cognitive performances (including memory) is significantly prevented by the combinations of the invention.

Furthermore, the FIG. 16 shows that extremely low dose of Baclofen (480 μg/kg/day), Acamprosate (32 μg/kg/day) and Donepezil (0.25 mg/kg/day) can be combined to allow a complete protection of behavioral and cognitive performances of mice as measured by Y-maze test. Whereas donepezil, at this concentration, have no significant effect (32% protection) on spatial working memory, its use in conjunction with the baclofen and acamprosate combination allows a complete protection (98%) of intoxicated mice's cognitive performances. Combinations of the invention can thus be further combined with other therapies in order to potentiate their action.

Combinations Improve Neurophysiological Concern of Neurological Diseases

Combinations therapies are tested in the in vivo model of Aβ intoxication. Their effects on several parameters which are affected in neurological diseases are assessed:

Caspases 3 and 9 expression level, considered as an indicator of apoptosis,

Lipid peroxidation, considered as a marker for oxidative stress level,

GFAP expression assay, considered as a marker of the level of brain inflammation, Brain Blood Barrier integrity, Overall synapse integrity (synaptophysin ELISA).

Quantification of viable neurons in the Cal.

Brain Blood Barrier Integrity

Experimental design about animal intoxication by Aβ is the same that in part III. The potential protective effect of the combination therapies on the blood brain barrier (BBB) integrity is analyzed in mice injected intracerebroventricularly (i.c.v.) with oligomeric amyloid-β25-35 peptide (Aβ25-35) or scrambled Aβ25-35 control peptide (Sc.Aβ), 7 days after injection.

On day 7 after the $A\beta_{25\text{-}35}$ injection, animals are tested to determine the BBB integrity by using the EB (Evans Blue) method. EB dye is known to bind to serum albumin after peripheral injection and has been used as a tracer for serum albumin.

EB dye (2% in saline, 4 ml/kg) is injected intraperitoneal (i.p.) 3 h prior to the transcardiac perfusion. Mice are then anesthetized with i.p. 200 μl of pre-mix ketamine 80 mg/kg, xylazine 10 mg/kg, the chest is opened. Mice are perfused transcardially with 250 ml of saline for approximately 15 min until the fluid from the right atrium becomes colourless. After decapitation, the brain is removed and dissected out into three regions: cerebral cortex (left+right), hippocampus (left+right), diencephalon. Then, each brain region is weighed for quantitative measurement of EB-albumin extravasation.

Samples are homogenized in phosphate-buffered saline solution and mixed by vortexing after addition of 60% trichloroacetic acid to precipitate the protein. Samples are cooled at 4° C., and then centrifuged 30 min at 10,000 g, 4° C. The supernatant is measured at 610 nm for absorbance of EB using a spectrophotometer.

EB is quantified both as
μg/mg of brain tissue by using a standard curve, obtained by known concentration of EB-albumin.
μg/mg of protein.

Overall Synapse Integrity (Synaptophysin ELISA)

Synaptophysin has been chosen as a marker of synapse integrity and is assayed using a commercial ELISA kit (USCN, Ref. E90425Mu). Samples are prepared from hippocampus tissues and homogenized in an extraction buffer specific to as described by manufacturer and reference literature.

Tissues are rinsed in ice-cold PBS (0.02 mol/l, pH 7.0-7.2) to remove excess blood thoroughly and weighed before nitrogen freezing and −80° C. storage. Tissues are cut into small pieces and homogenized in 1 ml ice-cold phosphate buffer saline (PBS) solution with a glass homogenizer. The resulting suspension is sonicated with an ultrasonic cell disrupter or subjected to two freeze-thawing cycles to further break the cell membranes. Then, homogenates are centrifugated for 5 min at 5,000 g and the supernatant is assayed immediately.

All samples are assayed in triplicates.

Quantification of proteins is performed with the Pierce BCA (bicinchoninic acid) protein assay kit (Pierce, Ref. #23227) to evaluate extraction performance and allow normalization.

The total protein concentrations are then calculated from standard curve dilutions and serve to normalize ELISA results.

Quantification of Viable Neurons in the CAl

On day 8, each mouse is anesthetized with 200 μl i.p. of a pre-mix of ketamine 80 mg/kg and xylazine 10 mg/kg and transcardially perfused with 100 ml of saline solution followed by 100 ml of 4% paraformaldehyde. The brains are removed and kept for 24 h post-fixation in 4% paraformaldehyde solution at 4° C.

After post-fixation, brains are washed in a phosphate buffer saline (PBS) solution, then cerebellum is removed and the forebrains are placed on a vibratom plateform (Leica VT100OS, Leica, Wetzlar, Germany) for slicing.

Brains are cut in coronal sections (20 μm thickness) using a vibratom (Leica VT100OS, Leica, Wetzlar, Germany). Serial sections are placed on 24-well plate with PBS. They are then selected to include the hippocampal formation and 9 sections are placed in gelatin-coated glass-strip (one slide per animal for cresyl violet). All slides are dried at room temperature for 48 h to avoid unsticking. The slides are stored at room temperature until cresyl violet staining.

Sections are stained with 0.2% Cresyl violet reagent (Sigma-Aldrich), then dehydrated with graded ethanol, treated with toluene, and are mounted with Mountex medium (BDH Laboratory Supplies, Poole, Dorset, UK).

After mounting, slides are kept at RT for 24 h drying. Examination of the CA 1 area are performed using a light microscope (Dialux 22, Leitz), with slices digitalized through a CCD camera (Sony XC-77CE, Sony, Paris, France) with the NIHImage® v1.63 software (NIH). CAl measurement and pyramidal cells counts are processed using ImageJ® (NIH). Data are expressed as mean of nine slices of CA 1 pyramidal cells per millimeter for each group (left and right hippocampus CAl counting) (49).

Oxidative Stress Assay

Mice are sacrificed by decapitation and both hippocampi are rapidly removed, weighted and kept in liquid nitrogen until assayed. After thawing, hippocampus are homogenized in cold methanol (1/10 w/v), centrifuged at 1,000 g during 5 min and the supernatant placed in eppendorf tube. The reaction volume of each homogenate are added to FeSO4 1 mM, H2SO4 0.25 M, xylenol orange 1 mM and incubated for 30 min at room temperature. After reading the absorbance at 580 nm (A580 1), 10 µl of cumene hydroperoxide 1 mM (CHP) is added to the sample and incubated for 30 min at room temperature, to determine the maximal oxidation level. The absorbance is measured at 580 nm (A580 2). The level of lipid peroxidation is determined as CHP equivalents (CHPE) according to: CHPE=A580 1/A580 2×[CHP] and expressed as CHP equivalents per weight of tissue and as percentage of control group data.

Caspase Pathway Induction Assay and GFAP Expression Assay

Mice are sacrificed by decapitation and both hippocampi are rapidly removed, rinsed in ice-cold PBS (0.02 mol/l, pH 7.0-7.2) to remove excess blood thoroughly weighted and kept in liquid nitrogen until assayed. Tissues are cut into small pieces and homogenized in 1 ml ice-cold PBS with a glass homogenizer. The resulting suspension is sonicated with ultrasonic cell disrupter or subjected to two freeze-thawing cycles to further break the cell membranes. Then, homogenates are centrifugated at 5,000 g during 5 min and the supernatant is assayed immediately.

Experiments are conducted with commercial assay: Caspase-3 (USCN-E90626Mu), Caspase-9 (USCN-E90627Mu), GFAP (USCN-E90068).

Quantification of proteins is performed with the Pierce BCA (bicinchoninic acid) protein assay kit (Pierce, Ref. #23227) to evaluate extraction performance and allow normalization.

The combination of Baclofen and Acamprosate induces a significant protective effect on neurophysiological functions of intoxicated animals as shown in FIGS. 11, 12, 13 & 14.

Figure 13:
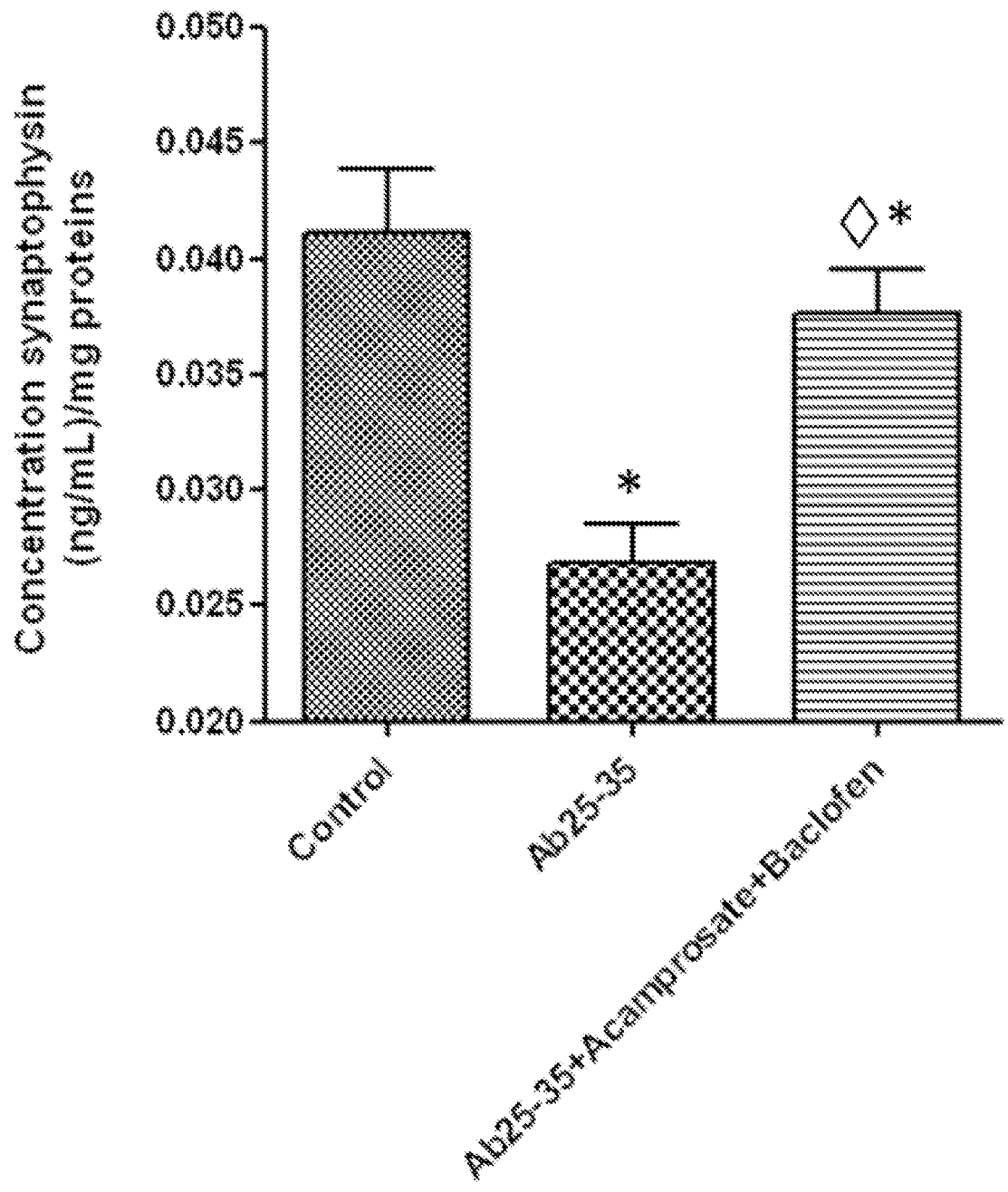
FIG. 13: Effect of Acamprosate and Baclofen combination therapy on the synaptic density as reflected by the synaptophysin concentration. The amyloid peptide affect the synapse function inducing a significant decrease the synaptophysin concentration in brain, above 34%, compared to control. Those damages on the synaptic density are significantly prevented (76%) by the combination of Acamprosate (0.2 mg/kg/day) and Baclofen (3 mg/kg/day). ◊: p<0.05, significantly different from $A\beta_{25-35}$ intoxication; *: p<0.05, significantly different from vehicle (ANOVA+Dunnett Post-Hoc test).

With a protection of more than 60% compared to non-treated intoxicated animals, the combination is effective for the protection of neurons (FIG. 11) and synaptic density (FIG. 13).

Figure 12:
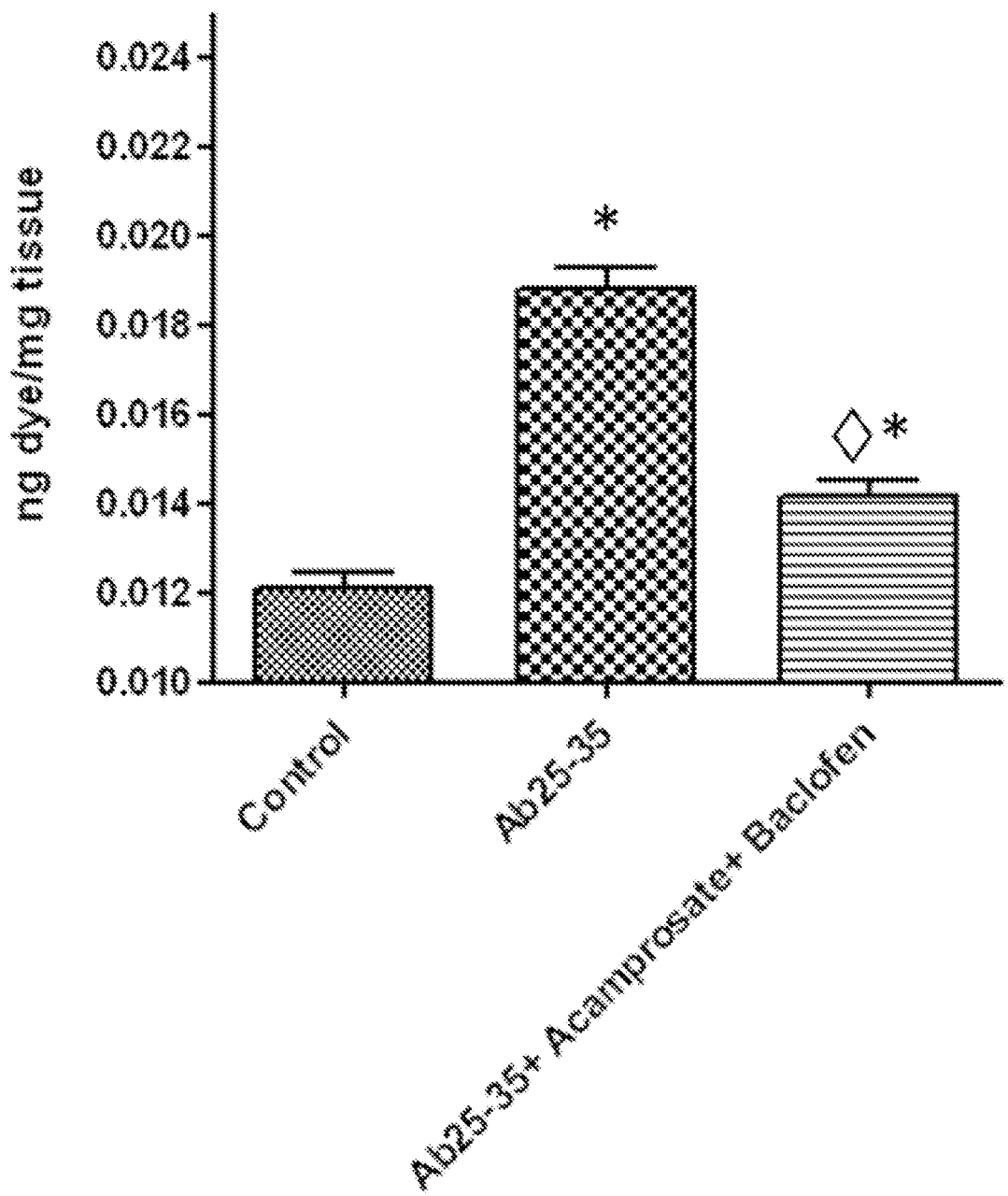
FIG. 12: Effect of Acamprosate and Baclofen combination therapy on the blood brain barrier integrity. The amyloid peptide affect the blood brain barrier (BBB) inducing a significant increase of its permeability, above 51%, compared to control. Those damages on the blood brain barrier are significantly prevented (66.6% of the integrity restored) by the combination of Acamprosate (0.2 mg/kg) and Baclofen (3 mg/kg). ◊: p<0.05, significantly different from $A\beta_{25-35}$ intoxication; *: p<0.05, significantly different from vehicle (ANOVA+Dunnett Post-Hoc test).

Similarly, FIG. 12 show that the combination of Baclofen and Acamprosate protect the BBB integrity (76%) compared with non-treated intoxicated animals.

Figure 14:
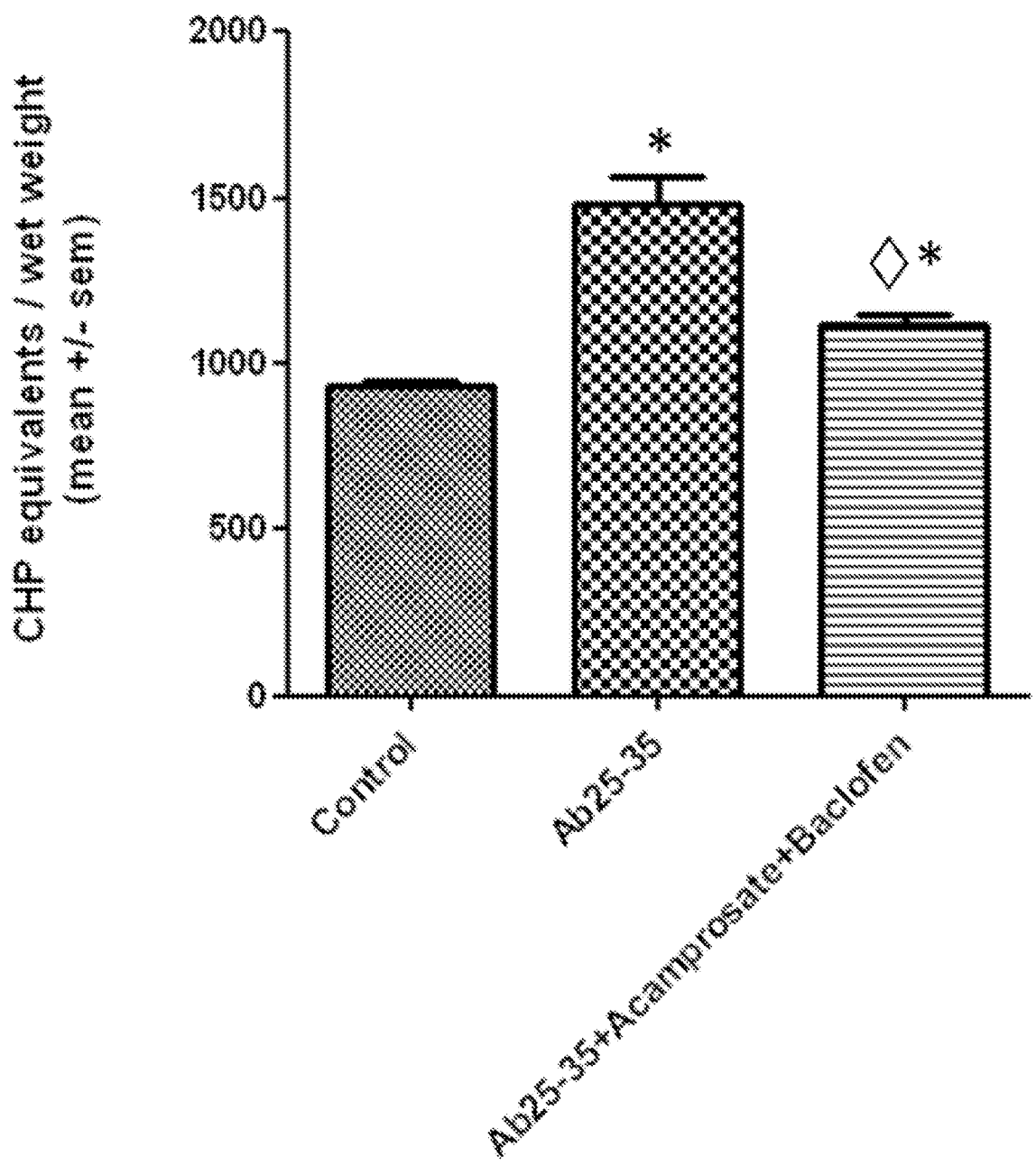
FIG. 14: Protective effect of Acamprosate and Baclofen combination therapy on the oxidative stress in hippocampus. The amyloid peptide induces a significant increase of oxidative stress in hippocampus as measured by lipid peroxydation, above 59%, compared to control. This oxidative stress is significantly prevented (65.9%) by the combination of Acamprosate (0.2 mg/kg/day) and Baclofen (3 mg/kg/day). ◊: p<0.05, significantly different from $A\beta_{25-35}$ intoxication; *: p<0.05, significantly different from vehicle (ANOVA+Dunnett Post-Hoc test).

Finally, this combination therapy is efficient in reducing the overall oxidative stress induced by Aβ in brain of treated animals when compared with the non-treated intoxicated animals (FIG. 14).

As shown in the Part A of examples, several neurological functions impaired in numerous neurological disorders, including neurodegenerative disorders such as Alzheimer disease and related disorders have been protected and symptoms retarded or reduced by the combination Baclofen-Acamprosate.

B) Prevention of Glutamate Toxicity on Neuronal Cells

In this further set of experiment, candidate compounds have been tested for their ability to prevent or reduce the toxic effects of glutamate toxicity on neuronal cells. Glutamate toxicity is involved in the pathogenesis of neurological diseases or disorder such as Multiple Sclerosis, Alzheimer's Disease, Amyotrophic Lateral Sclerosis, Parkinson's Disease, Huntington's Disease, neuropathies, alcoholism or alcohol withdrawal, or spinal cord injury. The drugs are first tested individually, followed by assays of their combinatorial action.

Methods

The efficacy of drug combinations of the invention is assessed on primary cortical neuron cells. The protocol which is used in these assays is the same as described in section A.I.2 above.

Glutamate Toxicity Assays

The neuroprotective effect of compounds is assessed by quantification of the neurite network (Neurofilament immunostaining (NF)) which specifically reveals the glutamatergic neurons.

After 12 days of neuron culture, drugs of the candidate combinations are solved in culture medium (+0.1% DMSO). Candidate combinations are then pre-incubated with neurons for 1 hour before the Glutamate injury. One hour after incubation with, Glutamate is added for 20 min, to a final concentration of 40 µM, in presence of candidate combinations, in order to avoid further drug dilutions. At the end of the incubation, medium is changed with medium with candidate combination but without glutamate. The culture is fixed 24 hours after glutamate injury. MK801 (Dizocilpinehydrogen maleate, 77086-22-7-20 µM) is used as a positive control.

After permeabilization with saponin (Sigma), cells are blocked for 2 h with PBS containing 10% goat serum, then the cells are incubated with mouse monoclonal primary antibody against Neurofilament antibody (NF, Sigma). This antibody is revealed with Alexa Fluor 488 goat anti-mouse IgG.

Nuclei of cells are labeled by a fluorescent marker (Hoechst solution, SIGMA), and neurite network quantified. Six wells per condition are used to assess neuronal survival in 3 different cultures.

Results

The combination Baclofen-Acamprosate give a protective effect against glutamate toxicity for cortical neuronal cells. As exemplified in FIG. 15, combinations of the invention strongly protect neurons from glutamate toxicity under experimental conditions described above. It is noteworthy that an effective protection is noticed using drug concentrations at which drugs used alone have lower protective effect. Combination of Baclofen and Acamprosate induce an improvement of more than 200% compared to acamprosate alone and more than 47% compared to baclofen used alone.

C) Improvement of Other Disorders Related to Glutamate Excitoxicity Using Combinations of the Invention The above mentioned in vitro protective effect against glutamate toxicity of drugs and drug combinations of the invention combined with the protective effects exemplified herein in several AD models, prompted the inventors to test these drugs and combinations in some models of other diseases in the pathogenesis of which glutamate toxicity is also involved, as MS, ALS and neuropathic pain.

I) Protective Effect of Combinations in an In Vivo Model of Multiple Sclerosis.

A model in which myelin-oligodendrocyte glycoprotein-immunized (MOG-immunized) mice develop chronic progressive EAE is used to demonstrate the beneficial effect of compositions of the invention in multiple sclerosis treatment.

Animals and Chemicals

C57L/6J female mice (8 weeks old) are purchased from Janvier (France); after two weeks of habituation, female mice (10 weeks old) develop chronic paralysis after immunization with MOG (Myelin Oligodendrocyte Glycoprotein) peptide. The experimental encephalomyelitis is induced with the Hooke Kit $MOG_{35-55}$/CFA Emulsion PTX (Pertussis toxin) for EAE Induction (EK-0110, EK-0115; Hooke laboratories). The control kit is CK-0115 (Hooke laboratories).

Experimental Procedure

The experimental encephalomyelitis is induced by following procedure:

The day 0, two subcutaneous injections of 0.1 ml each are performed; one on upper back of the mouse and one in lower back. Each injection contains 100 μg of MOG$_{35-55}$ peptide (MEVGWYRSPFSRVVHLYRNGK, SEQ ID NO:1), 200 μg of inactivated *Mycobacterium tuberculosis* H37Ra and is emulsified in Complete Freund's adjuvant (CFA) (Hooke laboratories). The emulsion provides antigen needed to expand and differentiate MOG-specific autoimmune T cells.

Two intraperitoneal injections of 500 ng of Pertussis toxin in PBS (Hooke kit) are performed 2 hours (Day 0) and 24 hours (Day 1) after the MOG injection. Pertussis toxin enhances EAE development by providing additional adjuvant.

Mice develop EAE 8 days after immunization and stay chronically paralyzed for the duration of the experiment. After the immunization, mice are daily observed for clinical symptoms in a blind procedure. Animals are kept in a conventional pathogen-free facility and all experiments are carried out in accordance with guidelines prescribed by, and are approved by, the standing local committee of bioethics.

Experimental Groups and Drug Treatment:

Groups of female mice as disclosed are homogenized by weight before the immunization:
- Control group: vehicle injection in the same conditions of EAE mice (from Day −1 to Day 28, placebo is given daily)
- EAE group: MOG injection (day 0)+Pertussis toxin injections (Day 0 and 1)—from Day −1 to Day 28, placebo is given orally daily
- EAE+positive control: MOG injection (Day 0)+Pertussis toxin injections (Day 0 and 1)—from Day −1 to Day 28, dexamethasone is given orally daily.
- EAE+treatment group: MOG injection (Day 0)+Pertussis toxin injections (Day 0 and 1). The treatments start one Day before immunization and last until Day 28.

The clinical scores are measured at Days 0-5-8-9-12-14-16-19-21-23-26-28.

Statistica software (Statsoft Inc.) is utilized throughout for statistical analysis. ANOVA analysis and Student's t test are employed to analyse clinical disease score. P<0.05 is considered significant.

Delays of disease occurrence, clinical score and delay of death, have been compared between each group to the reference 'immu' group with Kaplan-Meier curves and a Cox model (R package 'survival'). Resulting p-values are unilateral and test the hypothesis to be better than the reference 'immu' group.

The total clinical score is composed of the tail score, the hind limb score, the fore limb score and the bladder score described as below:

Tail Score:

| | |
|---|---|
| Score = 0 | A normal mouse holds its tail erect when moving. |
| Score = 1 | If the extremity of the tail is flaccid with a tendency to fall. |
| Score = 2 | If the tail is completely flaccid and drags on the table. |

Hind Limbs Score:

| | |
|---|---|
| Score = 0 | A normal mouse has an energetic walk and doesn't drag his paws |
| Score = 1 | Either one of the following tests is positive:<br>A - Flip test: while holding the tail between thumb and index finger, flip the animal on his back and observe the time it takes to right itself. A healthy mouse will turn itself immediately. A delay suggests hind-limb weakness.<br>B - Place the mouse on the wire cage top and observe as it crosses from one side to the other. If one or both limbs frequently slip between the bars we consider that there is a partial paralysis. |
| Score = 2 | Both previous tests are positive. |
| Score = 3 | One or both hind limbs show signs of paralysis but some movements are preserved; for example: the animal can grasp and hold on to the underside of the wire cage top for a short moment before letting go. |
| Score = 4 | When both hind legs are paralyzed and the mouse drags them when moving. |

Fore Limbs Score:

| | |
|---|---|
| Score = 0 | A normal mouse uses its front paws actively for grasping and walking and holds its head erect. |
| Score = 1 | Walking is possible but difficult due to a weakness in one or both of the paws, for example, the front paws are considered weak when the mouse has difficulty grasping the underside of the wire top cage. Another sign of weakness is head drooping. |
| Score = 2 | When one forelimb is paralyzed (impossibility to grasp and the mouse turns around the paralyzed limb). At this time the head has also lost much of its muscle tone. |
| Score = 3 | Mouse cannot move, and food and water are unattainable. |

Bladder Score:

| | |
|---|---|
| Score = 0 | A normal mouse has full control of its bladder. |
| Score = 1 | A mouse is considered incontinent when its lower body is soaked with urine. |

The global score for each animal is determined by the addition of all the above mentioned categories. The maximum score for live animals is 10.

Results-Combinations Therapies are Efficient in a MS Model

A significant improvement of global clinical score is observed in "EAE+ treatment group" mice for the Baclofen and Acamprosate combination.

Figure 18:
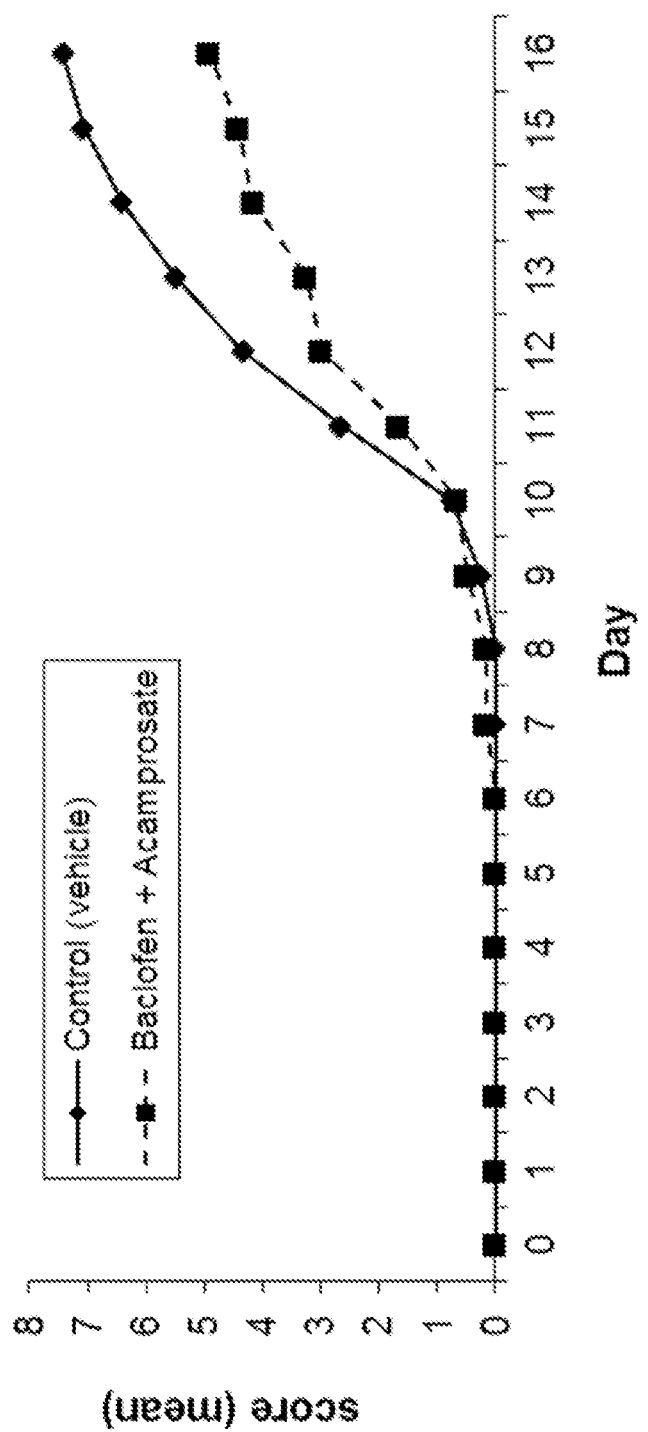
FIG. 18: Effect of Acamprosate and Baclofen combination therapy on the development of chronic progressive experimental autoimmune encephalomyelitis (EAE) as defined by clinical score. Immunization induces a significant decrease in physical features as measured by clinical score. This deleterious effect is significantly prevented (p-value<0.01) by the combination of Acamprosate (2 mg/kg/day) and Baclofen (30 mg/kg/day).

The combination of Baclofen (30 mg/kg/day) and Acamprosate (2 mg/kg/day) induced a significant protective effect against the development of chronic progressive EAE and hence confirmed the beneficial effect of the composition in multiple sclerosis treatment (FIG. 18). With more than 30% reduction of the symptoms, the results clearly show that the combination induces a significant reduction of disease development from day 13. This result confirms the remarkable positive effect of Baclofen-Acamprosate combination on the neuronal protection including on demyelination and its implications.

Taken together, these results show that this combination enables effective protection of neurons against many stresses involved in the development of neurological disease such as βamyloid, BBB breakdown, glutamate excitotoxicity or demyelination.

II. Protective Effect of Combinations in Models of ALS.

The effect of Combination therapies according to the present invention on ALS have been demonstrated in vitro, in a co-culture model, and in vivo, in a mouse model of ALS. Protocols and results are presented in this section.

II.1 Protective Effect Against Glutamate Toxicity in Primary Cultures of Nerve-Muscle Co-Culture Primary Co-Cultures of Nerve-and Muscle Cells Human muscle is prepared according to a previously described method from portions of biopsy of healthy patient (48). Muscle cells are established from dissociated cells (10000 cells per wells), plated in gelatin-coated 0.1% on 48 wells plate and grown in a proliferating medium consisting of mix of MEM medium and M199 medium.

Immediately after satellite cells fusion, whole transverse slices of 13-day-old rat Wistar embryos spinal cords with dorsal root ganglia (DRG) attached are placed on the muscle monolayer 1 explant per well (in center area). DRG are necessary to achieve a good ratio of innervations. Innervated cultures are maintained in mix medium. After 24 h in the usual co-culture neuritis are observed growing out of the spinal cord explants. They make contacts with myotubes and induce the first contractions after 8 days. Quickly thereafter, innervated muscle fibres located in proximity to the spinal cord explants, are virtually continuously contracting Innervated fibres are morphologically and spatially distinct from the non-innervated ones and could easily be distinguished from them.

One co-culture is done (6 wells per conditions).

Glutamate Injury

On day 27, co-cultures are incubated with candidate compounds or Riluzole one hour before glutamate intoxication (60 µM) for 20 min. Then, co-cultures are washed and candidate compounds or Riluzole are added for an additional 48 h. After this incubation time, unfixed co-cultures are incubated with α-bungarotoxin coupled with Alexa 488 at concentration 500 nmol/L for 15 min at room temperature. Then, co-cultures fixed by PFA for 20 min at room temperature. After permeabilization with 0.1% of saponin, co-cultures are incubated with anti-neurofilament antibody (NF).

These antibodies are detected with Alexa Fluor 568 goat anti-mouse IgG (Molecular probe). Nuclei of neurons are labeled by a fluorescent marker (Hoechst solution).

Endpoints are (1) Total neurite length, (2) Number of motor units, (3) Total motor unit area, which are indicative of motor-neurone survival and functionality.

For each condition, 2×10 pictures per well are taken using InCell Analyzer™ 1000 (GE Healthcare) with 20× magnification. All the images are taken in the same conditions.

Results

Baclofen and Acamprosate combination effectively protect motor neurones and motor units in the co-culture model.

II.2—Combinations Therapies are Efficient in ALS Mouse Model

Experiments are performed on male mice. Transgenic male mice B6SJL-Tg(SOD1)2Gur/J mice and their control (respectively SN2726 and SN2297 from Jackson Laboratories, Ben Harbor, USA and distributed by Charles River in France) are chosen in this set of experiments to mimic ALS.

Diseased mice express the SOD1-G93A transgene, designed with a mutant human SOD1 gene (a single amino acid substitution of glycine to alanine at codon 93) driven by its endogenous human SOD1 promoter. Control mice express the control human SOD1 gene.

Randomisation of the Animals:

The group assignation and the randomisation of the animals are based on the body weight; for each group, the randomisation is done one day before the first treatment.

Drug Administration

Mice are dosed with candidate drug treatment diluted in vehicle from 60th day after birth till death. Diluted solutions of drug candidates are prepared with water at room temperature just before the beginning of the administration.

In drinking water:

Riluzole is added in drinking water at a final concentration of 6 mg/ml (adjusted to each group mean body weight) in 5% cyclodextrin. As a mouse drinks about 5 ml/day, the estimated administrated dose is 30 mg/kg/day which is a dose that was shown to increase the survival of mice.

Cyclodextrine is used as vehicle at the final concentration of 5%, diluted in water at room temperature from stock solution (cyclodextrin 20%).

Oral administration (per os):

Drug combinations are administrated per os, daily.

Cyclodextrine is used as vehicle at the final concentration of 5%, diluted in water at room temperature from stock solution (cyclodextrin 20%).

Clinical Observation

The clinical observation of each mouse is performed daily, from the first day of treatment (60 days of age) until the death (or sacrifice). Clinical observation consists in studying behavioural tests: onset of paralysis, "loss of splay", "loss of righting reflex", and general gait observation:

Onset of paralysis: The observation consists of paralysis observation of each limb. Onset of paralysis corresponds to the day of the first signs of paralysis.

The loss of splay test consists of tremors or shaking notification and the position of hind limb (hanging or splaying out) when the mouse is suspended by the tail.

The loss of righting reflex test evaluates the ability of the mouse to right itself within 30 sec of being turned on either side. The righting reflex is lost when the mouse is unable to right itself. The loss of righting reflex determines the end stage of disease: the mouse unable to right itself is euthanized.

Results-Combinations Therapies are Efficient in ALS In Vivo Model

An improvement of the disease is observed for the diseased animals treated with for the Baclofen and Acamprosate combination.

III) Protective Effect of Combinations in Oxaliplatine Induced Neuropathy as an In Vivo Model for Neuropathic Pain.

Combinatorial therapies of the present invention are tested in vivo, in suitable models of peripheral neuropathy, i.e., acute model of oxaliplatin-induced neuropathy and chronic model of oxaliplatin-induced neuropathy. The animals, protocols and results are presented in this section.

Animal Husbandry

Sprague-Dawley rats (CERJ, France), weighing 150-175 g at the beginning of the experimental of the Oxaliplatin treatment ($D_0$) are used. Animals are housed in a limited access animal facility in a temperature (19.5° C.-24.5° C.) and relative humidity (45%-65%) controlled room with a 12 h-light/dark cycle, with ad libitum access to standard pelleted laboratory chow and water throughout the study. Animals are housed 4 or 5 per cage and a one week-acclimation period is observed before any testing.

Experimental Design

Four following groups of rats are used in all experiments:

Control Groups:

Group 1: Vehicle of Oxaliplatin (distilled water), i.p./Vehicle of candidate combination(s) (Distilled water), p.o. daily.

Group 2: Oxaliplatin (distilled water), i.p./Vehicle of candidate combination(s) (Distilled water), p.o. daily.

Group 3: Oxaliplatin 3 mg/kg i.p./single drug in Distilled water, p.o. daily×9.

Tested Composition Groups:

Group 4: Oxaliplatin 3 mg/kg i.p./candidate combination(s) in Distilled water, p.o. daily×9.

Group 5: Oxaliplatin 3 mg/kg i.p./Gabapentin (100 mg/kg) in Distilled water, p.o. on testing days (i.e. $D_1$ & $D_8$);

Vehicle and test items are delivered daily from D-1 to D7 (the day before the last testing day) whereas Gabapentin is administered on testing days (120 minutes before the test).

All treatments are administered in a coded and random order when it is possible. Doses are expressed in terms of free active substance.

Neuropathy Induction

Acute neuropathy is induced by a single intraperitoneal injection of oxaliplatin (3 mg/kg).

Chronic peripheral neuropathy is induced by repeated intraperitoneal injections of oxaliplatin (3 mg/kg, i.p.) on days 0, 2, 4 and 7 (CD=12 mg/kg, i.p.). Chronic neuropathy in humans is cumulative as well and is most commonly seen in patients who have received total doses of oxaliplatin > or =540 mg/m$^2$ which corresponds to ~15 mg/kg as cumulative dose in rats (Cersosimo R. J. 2005).

The oxaliplatin-induced painful neuropathy in rat reproduces the pain symptoms in oxaliplatin-treated patients:
- The thermal hyperalgesia is the earliest symptom. It can be measured with the acetone test or with the tail-immersion test;
- The mechanical hyperalgesia appears later. It can be quantified with the Von Frey test or the paw pressure test.

Animal Dosing and Testing

All drug combinations are administered from the day before the first intraperitoneal injection of oxaliplatin 3 mg/kg (D-1) and pursued daily orally until D7. During the testing days (i.e. D1 and D7), the drug combinations are administered after the test. Animals from the reference-treated group (gabapentin) are dosed only during the testing days.

Acetone Test

Cold allodynia is assessed using the acetone test by measuring the responses to thermal non-nociceptive stimulation on D1 (around 24 h after the first injection of oxaliplatin 3 mg/kg (acute effect of oxaliplatin), and D8 (chronic effect of oxaliplatin).

In the acetone test, latency of hindpaw withdrawal is measured after application of a drop of acetone to the plantar surface of both hindpaws (reaction time) and the intensity of the response is scored (cold score). Reaction time to the cooling effect of acetone is measured within 20 sec (cut-off) after acetone application. Responses to acetone are also graded to the following 4-point scale: 0 (no response); 1 (quick withdrawal, flick of the paw); 2 (prolonged withdrawal or marked flicking of the paw); 3 (repeated flicking of the paw with licking or biting).

For each experimental group, results are expressed as:
- The reaction time defined as the time expressed in sec required to elicit paw reaction (mean of 6 measures for each rat together±SEM).
- The cumulative cold score defined as the sum of the 6 scores for each rat together±SEM. The minimum score being 0 (no response to any of the 6 trials) and the maximum possible score being 18 (repeated flicking and licking or biting of paws on each of the six trials).

Statistical Analyses

Student test, unilateral, type 3 is performed. The significance level is set as p<0.05; all the groups are compared to the diseased+vehicle group (oxaliplatin treated group). Means and standard error mean are shown on the figures.

Results

Oxaliplatin induced a significant decrease in reaction time of paw withdrawal after acetone application (diseased group+vehicle) during the time course. This decrease is progressive and significant from day 1 (acute model of oxaliplatin-induced neuropathy) to day 8 (chronic model) as compared to the vehicle group.

Anti-Allodynic Effect in Acute Model and Chronic Model of Oxaliplatin-Induced Neuropathy Baclofen and Acamprosate combination are tested in both models of oxaliplatin-induced neuropathy. It induces a significant decrease in the cumulative cold score and a significant increase of reaction time as compared to the oxaliplatin-vehicle treated group. In conclusion, this drug combination protects from chronic and acute neuropathy.

REFERENCES

1. Crook R. et al. (1998). A variant of Alzheimer's disease with spastic paraparesis and unusual plaques due to deletion of exon 9 of presenilin 1. *Nat. Med.* 4(4): 452-5.
2. Houlden H., Baker M., et al. (2000). Variant Alzheimer's disease with spastic paraparesis and cotton wool plaques is caused by PS-1 mutations that lead to exceptionally high amyloid-beta concentrations. *Ann Neurol.* 48(5): 806-8.
3. Kwok J. B., Taddei K., et al. (1997). Two novel presenilin-1 mutations in early-onset Alzheimer's disease pedigrees and preliminary evidence for association of presenilin-1 mutations with a novel phenotype. *Neuroreport.* 8(6): 1537-42.
4. Verkkoniemi A., Kalimo H., et al. (2001). Variant Alzheimer disease with spastic paraparesis: neuropathological phenotype. *J Neuropathol Exp Neurol.* 60(5): 483-92.
5. Citron M. (2004). Strategies for disease modification in Alzheimer's disease. *Nat Rev Neurosci.* 5(9): 677-85.
6. Suh Y. H. and Checker F. (2002). Amyloid precursor protein, presenilins, and alpha-synuclein: molecular pathogenesis and pharmacological applications in Alzheimer's disease. *Pharmacol Rev.* 54(3): 469-525.
7. Blacker D., Albert M. S., et al. (1994). Reliability and validity of NINCDS-ADRDA criteria for Alzheimer's disease. The National Institute of Mental Health Genetics Initiative. *Arch Neurol.* 51(12): 1198-204.
8. Rossor M. N., Fox N. C., et al. (1996). Clinical features of sporadic and familial Alzheimer's disease. *Neurodegeneration.* 5(4): 393-7.
9. Glenner G. G., Wong C. W., et al. (1984). The amyloid deposits in Alzheimer's disease: their nature and pathogenesis. *Appl Pathol.* 2(6): 357-69.
10. Ballatore C., Lee V. M., et al. (2007). Tau-mediated neurodegeneration in Alzheimer's disease and related disorders. Nat Rev Neurosci. 8(9): 663-72.
11. Bell K. F. and Claudio Cuello A. (2006). Altered synaptic function in Alzheimer's disease. *Eur J Pharmacol.* 545(1): 11-21.
12. Hardy J. A. and Higgins G. A. (1992). Alzheimer's disease: the amyloid cascade hypothesis. *Science.* 256(5054): 184-5.
13. Braak H. and Braak E. (1991). Neuropathological staging of Alzheimer-related changes. *Acta Neuropathol.* 82(4): 239-59.
14. Golde T. E. (2005). The Abeta hypothesis: leading us to rationally-designed therapeutic strategies for the treatment or prevention of Alzheimer disease. *Brain Pathol.* 15(1): 84-7.
15. Hardy J. and Selkoe D. J. (2002). The amyloid hypothesis of Alzheimer's disease: progress and problems on the road to therapeutics. *Science.* 297(5580): 353-6.
16. Selkoe D. J. (2000). The genetics and molecular pathology of Alzheimer's disease: roles of amyloid and the presenilins. *Neurol Clin.* 18(4): 903-22.

17. Zlokovic B. V., The Blood Brain Barrier In Health And Chronic Neurodegenerative Disorders. *Neuron review.* 2008, 57, 178-201.
18. Budd Haeberlein, S. L. and S. A. Lipton, Excitotoxicity in neurodegenerative disease, in *Encyclopedia of neuroscience*, L. R. Squire, Editor. 2009, Elsevier. p. 77-86.
19. Hughes, J. R., *Alcohol withdrawal seizures.* Epilepsy Behav, 2009. 15(2): p. 92-7.
20. Kim, A. H., G. A. Kerchner, and C. D W, *Blocking Excitotoxicity*, in *CNS Neuroprotection*, F. W. Marcoux and D. W. Choi, Editors. 2002, Springer: New York. p. 3-36.
21. Hama A, Sagen J., Antinociceptive effect of riluzole in rats with neuropathic spinal cord injury pain. J. Neurotrauma. 2011 January; 28(1):127-34.
22. Malgouris, C., et al., *Riluzole, a novel antiglutamate, prevents memory loss and hippocampal neuronal damage in ischemic gerbils.* J Neurosci, 1989. 9(11): p. 3720-7.
23. Wahl, F., et al., *Effect of riluzole on focal cerebral ischemia in rats.* Eur J Pharmacol, 1993. 230(2): p. 209-14.
24. Wahl, F., et al., *Riluzole reduces brain lesions and improves neurological function in rats after a traumatic brain injury.* Brain Res, 1997. 756(1-2): p. 247-55.
25. McGleenon B. M., Dynan K. B. and Passmore A. P. (1999). Acetylcholinesterase inhibitors in Alzheimer's disease. *Br J Clin Pharmacol.* 48(4): 471-480.
26. Parsons C. G., Danysz W, Quack G. (1999). Memantine is a clinically well tolerated N-methyl-D-aspartate (NMDA) receptor antagonist—a review of preclinical data. *Neuropharmacology.* 38(6):735-67.
27. Magnaghi V, et al. GABA receptor-mediated effects in the peripheral nervous system: a cross-interaction with neuroactive steroids. *Journal of Molecular Neuroscience.* 2006, 28:89-102.
28. Ettmayer, P., Amidon, G. L., Clement, B. & Testa, B. Lessons learned from marketed and investigational prodrugs. *J. Med. Chem.* 47, 2393-2404 (2004).
29. Beaumont, K., Webster, R., Gardner, I. & Dack, K. Design of ester prodrugs to enhance oral absorption of poorly permeable compounds: challenges to the discovery scientist. *Curr. Drug Metab.* 4, 461-485 (2003).
30. Heimbach, T. et al. Enzyme-mediated precipitation of parent drugs from their phosphate prodrugs. *Int. J. Pharm.* 261, 81-92 (2003).
31. Yang, C. Y., Dantzig, A. H. & Pidgeon, C. Intestinal peptide transport systems and oral drug availability. *Pharm. Res.* 16, 1331-1343 (1999).
32. Steffansen, B. et al. Intestinal solute carriers: an overview of trends and strategies for improving oral drug absorption. *Eur. J. Pharm. Sci.* 21, 3-16 (2004).
33. Stella, V. et al. Prodrugs: Challenges and Rewards (AAPS, New York, 2007).
34. Wermuth, C G. The Practice of Medicinal Chemistry. (Hardbound, 2003). Part VI, Chap 33: Designing prodrugs and bioprecursors.
35. Pezron, I. et al. Prodrug strategies in nasal drug delivery. *Expert Opin. Ther. Pat.*, Vol. 12, No. 3, 331-340 (2002).
36. Stella, V. J. Prodrugs as therapeutics. *Expert Opin. Ther. Pat.* 14, 277-280 (2004).
37. Stella, V. J. & Nti-Addae, K. W. Prodrug strategies to overcome poor water solubility. *Adv. Drug Deliv. Rev.* 59, 677-694 (2007).
38. Higuchi, T.; Stella, V. eds. Prodrugs As Novel Drug Delivery Systems. *ACS Symposium Series.* American Chemical Society: Washington, D.C. (1975). 31.
39. Roche, E. B. Design of Biopharmaceutical Properties through Prodrugs and Analogs. *American Pharmaceutical Association*: Washington, D.C. (1977).
40. Lal, R., et al., Arbaclofen placarbil, a novel R-baclofen prodrug: improved absorption, distribution, metabolism, and elimination properties compared with R-baclofen. J Pharmacol Exp Ther, 2009. 330(3): p. 911-21.
41. Feng Xu, Ge Peng, Thu Phan, Usha Dilip, Jian Lu Chen, Tania Chemov-Rogan, Xuexiang Zhang, Kent Grindstaff, Thamil Annamalai, Kerry Koller, Mark A. Gallop, David J. Wustrow, *Discovery of a novel potent GABAB receptor agonist*; Bioorg Med Chem. Lett. 2011 Nov. 1; 21(21): 6582-5.
42. Andrew R. Leach, Valerie J. Gillet. An Introduction to Chemoinformatics. Springer 2007.
43. S. Asad Rahman, M. Bashton, G. L. Holliday, R. Schrader and J. M. Thornton: Small Molecule Subgraph Detector (SMSD) Toolkit, Journal of Cheminformatics 2009, 1:12 doi:10.1186/1758-2946-1-12.
44. Stahl H., Wermuth C. G. (Eds.) Handbook of Pharmaceutical Salts: Properties, Selection, and Use. Wiley-VCH; 2 edition (Mar. 29, 2011).
45. Wishart D S, Knox C, Guo A C, Cheng D, Shrivastava S, Tzur D, Gautam B, Hassanali M. *DrugBank: a knowledgebase for drugs, drug actions and drug targets.* Nucleic Acids Res. 36, Issuesuppl 1. D901-D906 (2008).
46. Singer C. et al. Mitogen-activated protein kinase pathway mediates estrogen neuroprotection after glutamate toxicity in primary cortical neurons. *J. Neuroscience,* 1999, 19(7): 2455-2463.
47. Braun S, Croizatb B, Lagrangec M C, Wartera J M, Poindron P. *Neurotrophins increase motoneurons' ability to innervate skeletal muscle fibers in rat spinal cord-human muscle co-cultures.* Volume 136, Issues 1-2, March 1996, Pages 17-23.
48. Meunier J, Ieni J, Maurice T. *The anti-amnesic and neuroprotective effects of donepezil against amyloid ~25-35 peptide-induced toxicity in mice involve an interaction with the $G_1$ receptor.* Br J. Phamlacol. 149, 998-1012, 2006.

We claim:

1. A composition comprising a synergistic combination of baclofen and acamprosate or pharmaceutically acceptable salts thereof.

2. The composition of claim 1, said composition further comprising donepezil.

3. The composition of claim 1, wherein the compounds are mixed with a pharmaceutically acceptable carrier or excipient.

4. The composition of claim 1, wherein the ratio acamprosate/baclofen (W:W) is between 0.1 and 1000.

5. The composition of claim 1, which comprises a unit dose of baclofen of less than 100 mg.

6. The composition of claim 1, which comprises a unit dose of acamprosate of less than 400 mg.

7. The composition of claim 1, which comprises a calcium salt of acamprosate.

8. The composition of claim 1, which comprises baclofen and acamprosate as the only active agents.

9. A composition comprising synergistically effective amounts of baclofen and acamprosate or pharmaceutically acceptable salts thereof, mixed with a pharmaceutically acceptable carrier or excipient, acamprosate being at a unit-dose of less than 400 mg.

10. A composition comprising, mixed in a unit-dose with a pharmaceutically acceptable carrier or excipient, baclofen or a pharmaceutically acceptable salt thereof in a unit-dose of less than 100 mg and acamprosate or a pharmaceutically acceptable salt thereof in a unit-dose of less than 400 mg, wherein the unit-doses of baclofen and acamprosate are provided in synergistically effective amounts.

* * * * *

UNITED STATES PATENT AND TRADEMARK OFFICE
CERTIFICATE OF CORRECTION

PATENT NO. : 8,865,769 B2
APPLICATION NO. : 13/691981
DATED : October 21, 2014
INVENTOR(S) : Daniel Cohen et al.

It is certified that error appears in the above-identified patent and that said Letters Patent is hereby corrected as shown below:

In the Specification

Column 7,
Line 23, "nerves or neurons injuries" should read --nerve or neuron injuries--.

Column 9,
Lines 24-25, "as teached by" should read --as taught by--.

Column 10,
Line 67, "WO2009033054 WO2009052191" should read
 --WO2009033054, WO2009052191--.

Column 23,
Line 1, "Amyloid-α1-42" should read --Amyloid-β1-42--.

Column 24,
Lines 65-66, "neurites of neurons of neurons (MAP2)" should read
 --neurites of neurons (MAP2)--.

Column 26,
Line 55, "icy injection." should read --icv injection.--.

Column 27,
Line 20, "have no significant" should read --has no significant--.
Line 44, "the same that in" should read --the same as that in--.

Column 36,
Line 32, "Checker F." should read --Checler F.--.

Signed and Sealed this
Second Day of June, 2015

Michelle K. Lee
*Director of the United States Patent and Trademark Office*

Column 38,
Line 21, "Chemov-Rogan," should read --Chernov-Rogan,--.